United States Patent
Koizumi et al.

(10) Patent No.: US 10,959,997 B2
(45) Date of Patent: Mar. 30, 2021

(54) COMBINED AGENT FOR CELL THERAPY OF CORNEAL ENDOTHELIAL CELL

(71) Applicants: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

(72) Inventors: Noriko Koizumi, Kyotanabe (JP); Naoki Okumura, Kyotanabe (JP); Shigeru Kinoshita, Kyoto (JP)

(73) Assignees: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

( * ) Notice: Subject to any disclaimer, the term of this patent is extended or adjusted under 35 U.S.C. 154(b) by 2 days.

(21) Appl. No.: 15/108,355

(22) PCT Filed: Dec. 27, 2013

(86) PCT No.: PCT/JP2013/085359
§ 371 (c)(1),
(2) Date: Jun. 27, 2016

(87) PCT Pub. No.: WO2015/097920
PCT Pub. Date: Jul. 2, 2015

(65) Prior Publication Data
US 2016/0317528 A1     Nov. 3, 2016

(51) Int. Cl.
| | |
|---|---|
| A61K 31/4745 | (2006.01) |
| A61K 35/44 | (2015.01) |
| A61K 35/30 | (2015.01) |
| A61K 45/06 | (2006.01) |
| A61K 9/00 | (2006.01) |

(52) U.S. Cl.
CPC ........ *A61K 31/4745* (2013.01); *A61K 9/0048* (2013.01); *A61K 35/30* (2013.01); *A61K 35/44* (2013.01); *A61K 45/06* (2013.01)

(58) Field of Classification Search
None
See application file for complete search history.

(56) References Cited

U.S. PATENT DOCUMENTS

2010/0209402 A1* 8/2010 Koizumi .............. A61K 9/0048
424/93.7

FOREIGN PATENT DOCUMENTS

| JP | 2010-505001 A | 2/2010 |
|---|---|---|
| JP | 2012-518415 A | 8/2012 |
| JP | 2013-507936 A | 3/2013 |
| JP | 2013-515676 A | 5/2013 |
| JP | 2013-541344 A | 11/2013 |
| WO | WO 2008/103191 A1 | 8/2008 |
| WO | WO 2009/028631 A1 | 5/2009 |
| WO | WO 2010/096746 A1 | 8/2010 |
| WO | WO 2011/056416 A2 | 5/2011 |
| WO | WO 2011/080984 A1 | 7/2011 |
| WO | WO 2011/081221 A1 | 7/2011 |
| WO | WO 2012/062819 A2 | 5/2012 |
| WO | WO 2013/100208 A1 | 7/2013 |

OTHER PUBLICATIONS

Sen et al., Up-regulation of Paxillin and Focal Adhesion Signaling follows Dystroglycan Complex deletions and promotes a Hypertensive State of Differentiation, Eur J Cell Biol. 2011 ; 90(2-3): 249-260. doi:10.1016/j.ejcb.2010.06.005.*
Pasapera, Myosin II activity regulates vinculin recruitment to focal adhesions through FAK-mediated paxillin phosphorylation, J. Cell Biol. vol. 188 No. 6 877-890, 2010.*
Zaidel-Bar, A paxillin tyrosine phosphorylation switch regulates the assembly and form of cell-matrix adhesions, Journal of Cell Science 120, 137-148, 2007.*
Ramachandran, Rho-Rho kinase pathway in the actomyosin contraction and cellmatrix adhesion in immortalized human trabecular meshwork cells, Molecular Vision 2011; 17:1877-1890.*
Ramachandran et al., "Formation and Disassembly of Adherens and Tight Junctions in the Corneal Endothelium: Regulation by Actomyosin Contraction," *Investigative Ophthalmology & Visual Science*, 51(4): 2139-2148 (2010).
Japanese Patent Office, International Search Report in International Patent Application No. PCT/JP2013/085359 dated (Mar. 25, 2014).

* cited by examiner

*Primary Examiner* — Blaine Lankford
(74) *Attorney, Agent, or Firm* — Leydig, Voit & Mayer, Ltd.

(57) ABSTRACT

The present invention provides an agent for treating or preventing a disease, a disorder or a condition of a corneal endothelium, said agent comprising a corneal endothelial cell and a myosin II-specific inhibitor. More specifically, the myosin II-specific inhibitor is blebbistatin. The disease, the disorder or the condition is typically a disorder associated with Fuchs endothelial corneal dystrophy or corneal endothelial dysfunction (bullous keratopathy). Also provided is a method for treating or preventing a corneal endothelial disease, said method comprising a step of administering an effective amount of a myosin II-specific inhibitor together with a corneal endothelial cell to a subject.

8 Claims, 12 Drawing Sheets

COMBINED AGENT FOR CELL THERAPY OF CORNEAL ENDOTHELIAL CELL

CROSS-REFERENCE TO RELATED APPLICATIONS

This patent application is the U.S. national phase of International Patent Application No. PCT/JP2013/085359, filed Dec. 27, 2013, which is incorporated by reference in its entirety herein.

TECHNICAL FIELD

The present invention relates to a technique, a method, an agent and the like for treating or preventing a disease, disorder or condition of a corneal endothelium, and more specifically to a combined agent for treating corneal endothelial cells.

BACKGROUND ART

Visual information is recognized when light transmitted into the cornea, which is a transparent tissue at the frontmost part of an eyeball, reaches the retina and excites nerve cells of the retina, and a generated electric signal is transmitted through the optic nerve to the visual cortex of the cerebrum. To attain good vision, it is necessary that the cornea is transparent. The transparency of the cornea is maintained by holding the water content constant with pumping and barrier functions of corneal endothelial cells.

Human corneal endothelial cells are present at a density of about 3000 cells per 1 $mm^2$ at birth. Once damaged, human corneal endothelial cells have very limited ability to regenerate. For example, Fuchs' endothelial corneal dystrophy is a disease causing abnormality in endothelial cells inside the cornea, resulting in edema of the cornea. The cause thereof is unknown. In Fuchs' endothelial corneal dystrophy, extracellular matrix such as collagen is deposited on a part of the back surface of a Descemet's membrane at the back of the cornea, resulting in hypertrophy of a corneal guttae and Descemet's membrane. Hypertrophy of the corneal guttae and Descemet's membrane is a cause of photophobia or blurred vision in Fuchs' endothelial corneal dystrophy patients, which significantly compromises the QOL of the patients. It is understood that there is no effective therapeutic method other than corneal transplantation for Fuchs' endothelial corneal dystrophy. However, there is a shortage in cornea donation in Japan, where the number of patients waiting for corneal transplantation is about 2600 whereas the number of corneal transplantations performed in Japan is approximately 1700 annually.

Development of a therapeutic drug for Fuchs' endothelial corneal dystrophy is limited. There is no therapeutic drug that is currently in clinical use. Hence, therapy must rely on corneal transplantation.

Non Patent Literatures 1-6 describe research on ROCK inhibitors.

CITATION LIST

Patent Literature

[PTL 1] Japanese National Phase PCT Laid-open Publication No. 2013-541344

Non Patent Literature

[NPL 1] Exp Cell Res: Vol. 313, No. 16, Page. 3616-3623 (Oct. 10, 2007)
[NPL 2] Am J Pathol: Vol. 181, No. 1, Page. 268-277 (July 2012)
[NPL 3] The Proceedings of the Japan Cornea Conference 2013 page 38, Oral Presentation 5, Naihi Kiso [Foundation of Endothelium] 2020
[NPL 4] Journal of Clinical and Experimental Medicine: Vol. 241, No. 10, Page. 765-770 (Jun. 9, 2012)
[NPL 5] Int J Exp Pathol: Vol. 92, No. 3, Page. A15 (June 2011)
[NPL 6] The Science and Engineering Review of Doshisha University: Vol. 52, No. 4, Page. 261-266 (Jan. 31, 2012)

SUMMARY OF INVENTION

Solution to Problem

The inventors have discovered a technology in which a disease, disorder, or condition of a corneal endothelium can be treated or prevented by inhibiting myosin II, thereby completing the present invention. Thus, the present invention provides the following inventions.

(1) A medicament for treating or preventing a disease, disorder or condition of a corneal endothelium, comprising a corneal endothelial cell and a myosin II-specific inhibitor.
(2) The medicament of the treatment or prevention of item (1), wherein the myosin II-specific inhibitor is blebbistatin.
(3) The medicament of the treatment or prevention of item (1), wherein the disease, disorder or condition is a disorder related to Fuchs' endothelial corneal dystrophy or corneal endothelial dysfunction (bullous keratopathy).
(4) The medicament of the treatment or prevention of any one of items (1)-(3), wherein the disease, disorder or condition is due to a trauma or a surgical operation.
(5) The medicament of the treatment or prevention of any one of items (1)-(4), wherein the disease, disorder or condition is selected from the group consisting of photophobia, blurred vision, visual impairment, ophthalmalgia, epiphora, hyperemia, pain, eye discomfort, diminished contrast, glare, edema of the corneal stroma and corneal turbidity in bullous keratopathy.
(6) The medicament of the treatment or prevention of any one of items (1)-(5), wherein the corneal endothelium is from a primate.
(7) The medicament of the treatment or prevention of any one of items (1)-(6), wherein the corneal endothelium is from a human.
(8) The medicament of the treatment or prevention of any one of items (1)-(7), comprising an additional pharmaceutical ingredient.
(9) A medicament for treating or preventing a disease, disorder or condition of a corneal endothelium, comprising a myosin II-specific inhibitor.
(10) A medicament for treating or preventing a disease, disorder or condition of a corneal endothelium, comprising a myosin II-specific inhibitor, wherein the myosin II-specific inhibitor is administered in conjunction with a corneal endothelial cell.
(11) The medicament of the treatment or prevention of any one of items (9)-(10), which is an eye drop.
(A2) The medicament of the treatment or prevention of any one of items (9)-(11), wherein the myosin II-specific inhibitor is blebbistatin.
(A3) The medicament of the treatment or prevention of any one of items (9)-(11) and (A2), wherein the disease, disorder or condition is a disorder related to Fuchs' endothelial corneal dystrophy or corneal endothelial dysfunction (bullous keratopathy).

(A4) The medicament of the treatment or prevention of any one of items (9)-(11) and (A2)-(A3), wherein the disease, disorder or condition is due to a trauma or a surgical operation.
(A5) The medicament of the treatment or prevention of any one of items (9)-(11) and (A2)-(A4), wherein the disease, disorder or condition is selected from the group consisting of photophobia, blurred vision, visual impairment, ophthalmalgia, epiphora, hyperemia, pain, eye discomfort, diminished contrast, glare, edema of the corneal stroma and corneal turbidity in bullous keratopathy.
(A6) The medicament of the treatment or prevention of any one of items (9)-(11) and (A2)-(A5), wherein the corneal endothelium is from a primate.
(A7) The medicament of the treatment or prevention of any one of items (9)-(11) and (A2)-(A6), wherein the corneal endothelium is from a human.
(A8) The medicament of the treatment or prevention of any one of items (9)-(11) and (A2)-(A7), comprising an additional pharmaceutical ingredient.
(12) A myosin II-specific inhibiting substance for treating or preventing a corneal endothelial disease.
(13) A myosin II-specific inhibiting substance for treating or preventing a corneal endothelial disease, wherein the myosin II-specific inhibitor is administered in conjunction with a corneal endothelial cell.
(14) A method for treating or preventing a corneal endothelial disease, wherein the method comprises a step of administering an effective amount of myosin II-specific inhibitor in conjunction with a corneal endothelial cell to a subject.

In addition to the combinations expressly shown, it is intended that the one or more of the aforementioned features can be provided in further combinations in the present invention. Further embodiments and advantages of the present invention are recognized by those skilled in the art by reading and understanding the following Detailed Description as needed.

Advantageous Effects of Invention

The present invention provides a medicament that can treat or prevent a disease associated with the corneal endothelium by using a myosin II-specific inhibitor, where the technique can also be materialized as eye drops or the like. The present invention has drawn attention particularly as an invention that markedly improves the establishment of transplantation of a corneal endothelium.

The present invention has verified that therapy using a myosin II-specific inhibitor achieves the same level of effect as the ROCK inhibitor Y-27632 ((R)-(+)-trans-(4-pyridyl)-4-(1-aminoethyl)-dihydrochloride cyclohexanecarboxamide monohydrate). Y-27632 exhibits efficacy at 10-100 µM especially in animal models with bullous keratopathy, while the present invention exhibits efficacy at 1 µM, 3 µM and 10 µM. The present invention attains an effect of improving corneal transparency at the same level by suppressing a signaling pathway further downstream than Y-27632. Thus, it is expected that an effective medicament suppressing side effects is provided.

BRIEF DESCRIPTION OF DRAWINGS

FIG. 6 shows the thickness of cornea after transplantation of cultured corneal endothelial cells used in combination with blebbistatin. The X axis indicates the number of days (days) and the Y axis indicates the thickness of cornea (μm). The bold line and black circles indicate blebbistatin, and the dotted line and the white circles indicate Y-27632. The dosage and the like are the same as FIG. 5 and the like.

FIG. 7 shows the intraocular pressure after transplantation of cultured corneal endothelial cells used in combination with blebbistatin. The X axis indicates the number of days (days) and the Y axis indicates the intraocular pressure (mmHg). The bold line and black circles indicate blebbistatin, and the dotted line and the white circles indicate Y-27632. The dosage and the like are the same as FIG. 5 and the like.

DESCRIPTION OF EMBODIMENTS

Figure 1:
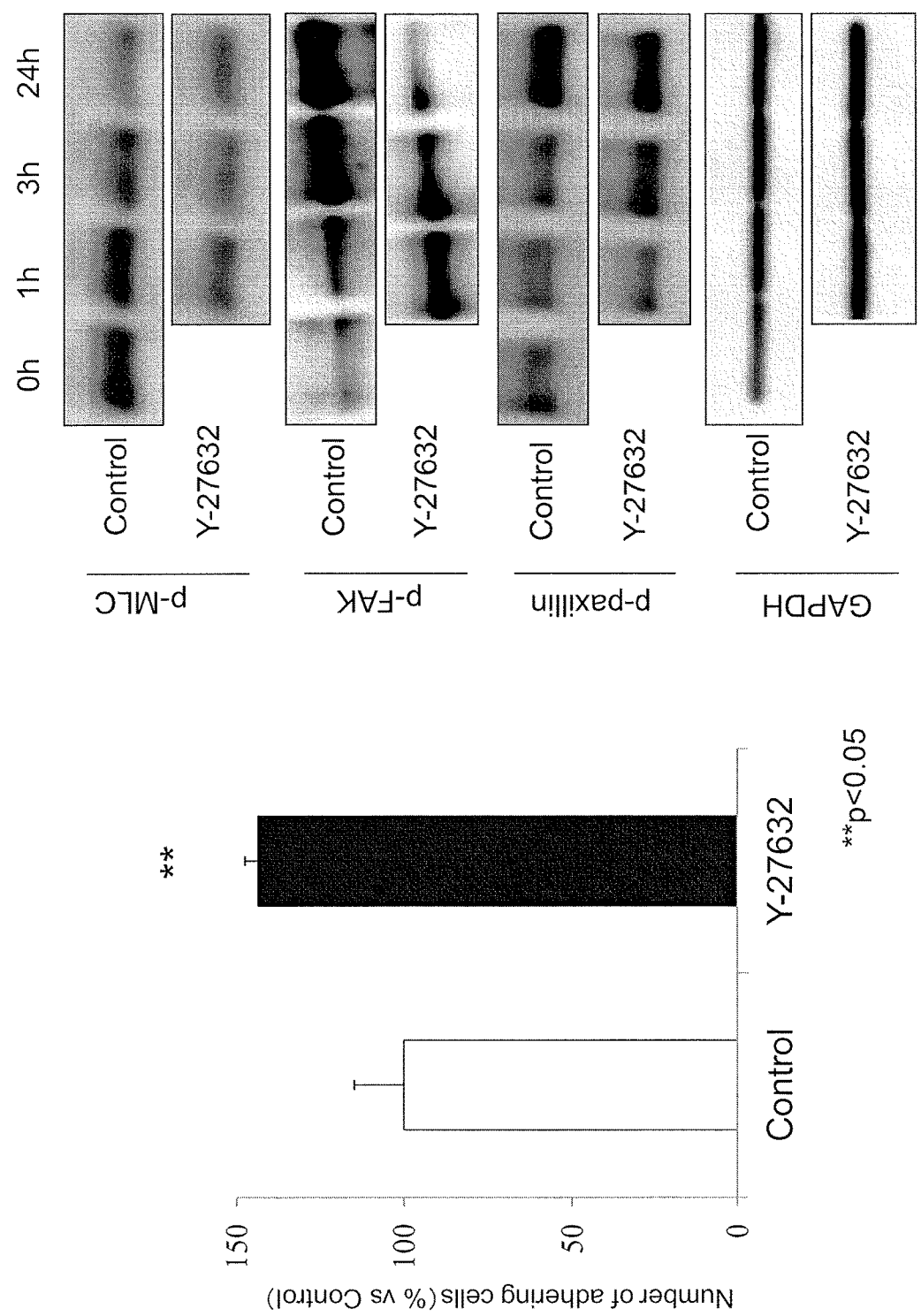
FIG. 1 shows results of examining cell adhesion and effect thereof on adhesion-related molecule due to a ROCK (Rho-associated coiled-coil forming kinase/Rho binding kinase) inhibitor and effects on adhesion-related molecules. The left diagram shows the results of examining cell adhesion due to a ROCK inhibitor by assessing the number of adhering cells with CellTiter-Glo®. It was found as a result that the number of adhering cells significantly increased when a ROCK inhibitor Y-27632 was added in comparison to the control. The right diagram shows results of measuring the activity of adhesion-related molecules and Rho-ROCK pathway after the addition of a ROCK inhibitor by Western blot. It was possible to verify that addition of Y-27632 suppresses phosphorylation of a myosin light chain (MLC). Further, it was possible to verify that adhesion-related molecules, focal adhesion kinase (FAK) and paxillin, are phosphorylated at an early stage.

The present invention is described hereinafter. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

Definition

As used herein, "myosin II-specific inhibitor" refers to any agent that specifically inhibits type II myosin. For such an inhibitor, those that inhibit myosin light chain (MLC) phosphorylation are particularly used. Examples of such an agent include, but are not limited to, blebbistatin (blebbistatin can be a (+) or (−) form enantiomer; (−) form has an effect while (+) form does not), myosin II-specific antibody, myosin IT-specific siRNA, myosin II-specific peptide aptamer, myosin II-specific antisense, myosin II-specific shRNA, myosin II-specific decoy and the like.

Examples of a myosin II inhibitor that can be used in the present invention further include, but are not limited to, the following. Go 7874, Hydrochloride (catalog number 365252), InSolution™ K-252a, Nocardiopsis sp. (catalog number 420297), K-252a, Nocardiopsis sp. (catalog number 420298), ML-7, Hydrochloride (catalog number 475880), ML-9, Hydrochloride (catalog number 475882), Myosin Light Chain Kinase Inhibitor Peptide 18 (catalog number 475981), Piceatannol (catalog number 527948), Staurosporine, Streptomyces sp. (catalog number 569397), W-12, Hydrochloride (catalog number 681635), W-13, Hydrochloride (catalog number 681636) (each of the above available from Merck Millipore), BDM (2,3-butanedione monoxime) (Used as a general myosin II inhibitor. Although it is known that BDM has action on skeletal muscle myosin II, BDM does not have an inhibiting effect on non-muscle myosin II, but rather is observed as inhibiting actin polymerization.) and the like. Specificity can be imparted to these inhibitors, when specificity is insufficient, by using a system for specific delivery.

As used herein, "myosin II" has the conventional meaning used in the art. Myosin II is a protein that regulates actin and is a complex consisting of a total of 6 polypeptide chains, i.e., 2 heavy chains each and 2 light chains for each heavy chain (required light chain (ELC; LC1; $MLC_{17}$) and regulatory light chain (RLC; LC2; $MLC_{20}$)). Heavy chains corresponding to three genes MYH9, MYH10 and MYH14 correspond to isoforms A, B, and C. Each individual heavy chain forms a complex with two types of light chains. Although not wishing to be bound by any theory, it is understood that any isoform in alignment with the objective of the present invention can be used for heavy chains and light chains. Although not wishing to be bound by any theory, it is understood that any agent can be used in the present invention as long as the myosin II function is suppressed or blocked. Although preferably not wishing to be bound by any theory, it is believed that an effect is exerted if the myosin light chain function is suppressed or blocked, especially if the phosphorylation thereof is suppressed or blocked. Thus, such an inhibitor is preferred, but the inhibitor is not limited thereto.

Myosin II-specific inhibitors suitable for use in the present invention also encompass functional mutants, mutants, derivatives and analogues of the aforementioned myosin II-specific inhibitors, as long as the ability to inhibit the activity or the mount of myosin II is maintained. "Variant", "derivative" and "analogue" as used herein refer to molecules having a similar form or structure as that of the parent compound and retaining the ability to act as a myosin II-specific inhibitor. For example, all of the myosin II-specific inhibitors disclosed herein may be crystallized. Useful analogues can be rationally designed based on coordinates responsible for shaping (one or more) active sites. Those skilled in the art can instead alter a known myosin II-specific inhibitor functional group or screen for such an altered molecule with an increase in activity, half-life, bioavailability or other desirable features without unnecessary experimentation. When myosin II-specific inhibitor is a polypeptide, fragments and variants of the polypeptide can be produced to increase ease of delivery, activity, half-life or the like (e.g., humanized antibody or functional antibody fragment as discussed above). Considering the technical level in the art for synthesizing and producing a recombinant polypeptide, such a variant may be achieved without undue experimentation. Those skilled in the art also may design a novel inhibitor based on the knowledge of the crystal structure and/or active site of a myosin II-specific inhibitor described herein. Myosin II-specific inhibitors may also be effectively introduced via gene transfer for polypeptides (antibody or the like). Thus, an embodiment of the method of the present invention comprises use of a vector suitable for the expression of a myosin II-specific inhibitor. In a preferred embodiment, administration of a myosin II-specific inhibitor can be accomplished by gene transfer using a vector comprising a cDNA encoding the myosin II-specific inhibitor. The vector induces in situ expression of the myosin II-specific inhibitor in cells to which the inhibitor is transfected with the vector. The myosin II activity is inhibited and myosin II mediated fibrosis is suppressed thereby. Any suitable vector may be used. Preferred vectors include an adenovirus vector, a lentivirus vector, an Epstein-Barr virus (EBV) vector, an adeno-associated virus (AAV) vector, and a retrovirus vector, developed for the purpose of gene transfer. Other non-vector methods for gene transfer may also be used, such as lipid/DNA complex, protein/DNA conjugate and naked DNA transfer methods.

In one exemplary embodiment, a myosin II-specific inhibitor is an antibody which blocks myosin II binding to a $F(ab)_2$ fragment, a Fv fragment, a single-stranded antibody, or a fragment of other "antibody" forms retaining the ability to bind to myosin II. Such an antibody may be chimerized or humanized. Herein, a chimerized antibody comprises a constant region of a human antibody and a variable region of a non-human antibody such as a mouse antibody. A humanized antibody comprises a constant region and a framework variable region (i.e., variable regions other than hypervariable regions) of a human antibody, and a hypervariable region of a non-human antibody such as a mouse antibody. As a matter of course, such an antibody may be any other type of antibody derivative, such as a human antibody selected or picked from a phage display system or produced from a XenoMouse.

As used herein, "substance (e.g., nucleic acid) for suppressing expression (of myosin II or the like)" is not particularly limited as long as it is a substance which suppresses transcription of an mRNA of a target gene, a substance (e.g., nucleic acid) which degrades a transcribed mRNA, or a substance (e.g., nucleic acid) which suppresses translation of a protein from an mRNA. Examples of such substances include siRNAs, antisense oligonucleotides, ribozyme, expression vectors thereof and other nucleic acids, among which a siRNA and expression vector thereof are preferred, and a siRNA is particularly preferred. "Substance which suppresses expression of a gene" includes proteins, peptides, and other small molecules in addition to those described above. It should be noted that a target gene in the present invention refers to any gene that is associated with a myosin II signaling pathway.

A method utilizing an antisense technique is well known to those skilled in the art as a method for inhibiting the expression of a specific endogenous gene such as myosin II, which is targeted in the present invention. As actions of an antisense nucleic acid that inhibit the expression of a target gene, there are a plurality of factors, i.e., inhibition of transcription initiation due to a triplex formation; inhibition of transcription due to hybrid formation with a site where an open loop structure is locally formed by RNA polymerase; inhibition of transcription due to hybrid formation with an RNA whose synthesis is about to progress; splicing inhibition due to hybrid formation at a junction of intron and exon; splicing inhibition due to hybrid formation with spliceosome formation site; inhibition of migration from a nucleus to cytoplasm due to hybrid formation with an mRNA; splicing inhibition due to hybrid formation with a capping site or a poly (A) addition site; inhibition of translation initiation due to hybrid formation with a translation initiation factor binding site; translational inhibition due to hybrid formation with a ribosome binding site near an initiation codon; inhibition of elongation of a peptide chain due to hybrid formation with a polysome binding site or a translation region of an mRNA; gene expression inhibition due to hybrid formation with an interaction site of a nucleic acid and a protein, and the like. In this manner, an antisense nucleic acid inhibits various processes, such as transcription, splicing and translation, to inhibit the expression of a target gene (Hirashima and Inoue, Shinsei Kagaku Jikken Kouza [*New Biochemical Experiment Course*] 2, Nucleic Acid, IV Idenshi no Fukusei to Hatsugen [*Replication and Expression of Gene*], Edited by the Japanese Biochemical Society, Tokyo Kagaku Dojin, 1993, 319-347).

The antisense nucleic acid used in the present invention may inhibit the expression and/or function of a gene (nucleic acid) encoding a member of a signaling pathway of the myosin II described above or the like by any of the above-described actions. In one embodiment, it is considered effective, for inhibiting translation of a gene, to design an antisense sequence complementary to a non-translation region near the 5' terminal of an mRNA of a gene encoding the myosin II described above or the like. Further, it is possible to use a sequence complementary to a coding region or a 3' non-translation region. In this manner, nucleic acids comprising an antisense sequence of a sequence of not only a translation region, but also a non-translation region of a gene encoding myosin II described above or the like are encompassed by the antisense nucleic acids that are used in the present invention. An antisense nucleic acid used is linked downstream of an appropriate promoter, and is preferably linked to a sequence comprising a transcription termination signal on the 3' end. A nucleic acid prepared in such a manner can be transformed into a desired animal (cell) using a known method. While the sequence of an antisense nucleic acid is preferably a sequence complementary to a gene encoding myosin II or the like of an animal (cell) to be transformed or a part thereof, it is not necessarily fully complementary as long as the sequence can effectively suppress the expression of genes. The transcribed RNA is preferably 90% or more, and most preferably 95% or more complementary to a transcription product of a target gene. In order to effectively inhibit the expression of a target gene using an antisense nucleic acid, the antisense nucleic acid is preferably at least 12 bases or more but less than 25 bases long. However, the antisense nucleic acid used in the present invention is not necessarily limited to this length. The length may be, for example, 11 bases or less, 100 bases or more, or 500 bases or more. While an antisense nucleic acid may be composed of only DNAs, it may also include nucleic acids other than DNAs, such as locked nucleic acid (LNA). In one embodiment, the antisense nucleic acid used in the present invention may be an LNA-containing antisense nucleic acid comprising LNA at the 5' terminal or the 3' terminal. In an embodiment where an antisense nucleic acid is used in the present invention, an antisense sequence can be designed based on a nucleic acid sequence of myosin II or the like using a method described in, for example, Hirashima and Inoue, Shinsei Kagaku Jikken Kouza [*New Biochemical Experiment Course*] 2, Nucleic Acid, IV Idenshino Fukuseito Hatsugen [*Replication and Expression of Gene*], Edited by the Japanese Biochemical Society, Tokyo Kagaku Dojin, 1993, 319-347.

The expression of myosin II or the like can also be inhibited by using ribozyme or a DNA encoding ribozyme. A ribozyme refers to an RNA molecule having catalytic activity. There are ribozymes with various types of activities, but researches focusing on a ribozyme as an enzyme for cleaving an RNA in particular have made it possible to design a ribozyme for cleaving an RNA in a site-specific manner. While there are ribozymes with 400 nucleotides or more in size, such as group I intron ribozymes and Ml RNA included in RNase P, there are also ribozymes having an activity domain of about 40 nucleotides, such as those referred to as hammer head and hairpin ribozymes (Makoto Koizumi and Eiko Ohtsuka, Protein Nucleic Acid And Enzyme, 1990, 35, 2191).

For example, the self-cleaving domain of a hammer head ribozyme cleaves the 3' side of C15 in a sequence called G13U14C15. The base-pair formation of U14 and A9 is considered important for the activity thereof. In addition, it is demonstrated that cleavage can be made at A15 or U15 instead of C15 (Koizumi, M. et al., FEBS Lett, 1988, 228, 228). A ribozyme with a substrate binding site complementary to an RNA sequence near a target site can be designed to create a restriction enzyme-like RNA cleaving ribozyme which recognizes a sequence such as UC, UU or UA in a target RNA (Koizumi, M. et al., FEBS Lett, 1988, 239, 285, Makoto Koizumi and Eiko Ohtsuka, Protein Nucleic Acid And Enzyme, 1990, 35, 2191, Koizumi, M. et al., Nucl. Acids Res., 1989, 17, 7059).

Further, hairpin ribozymes are also useful for the object of the present invention. Such a ribozyme is found in, for example, a negative strand of a satellite RNA of tobacco ringspot virus (Buzayan, J M., Nature, 1986, 323, 349.). It is also demonstrated that a target-specific RNA cleaving ribozyme can be created from hairpin ribozymes (Kikuchi, Y. & Sasaki, N., Nucl. Acids Res, 1991, 19, 6751, Kikuchi, Yo, Kagaku to Seibutsu [*Chemistry and Organism*], 1992, 30, 112.). In this manner, a transcription product of a gene encoding myosin II or the like can be specifically cleaved using a ribozyme to inhibit the expression of the gene.

Expression of an endogenous gene of myosin II or the like can also be suppressed by RNA interference (hereinafter, abbreviated as "RNAi") using a double-stranded RNA having a sequence identical or similar to a target gene sequence. RNAi is an approach that is currently drawing attention, where when a double-stranded RNA (dsRNA) is directly incorporated into a cell, expression of a gene having a sequence homologous to the dsRNA is suppressed. In mammalian cells, RNAi can be induced by using a short strand dsRNA (siRNA). In comparison to knockout mice, RNAi has many advantages, such as stable effect, easy experimentation, and low cost. SiRNAs are described in detail in other parts of the present specification.

As used herein, "siRNA" refers to an RNA molecule having a double-stranded RNA moiety consisting of 15 to 40 bases. A siRNA has a function of cleaving an mRNA of a target gene having a sequence complementary to an antisense strand of said siRNA to suppress the expression of the target gene. More specifically, the siRNA according to the present invention is an RNA comprising a double-stranded RNA moiety consisting of a sense RNA chain consisting of a sequence homologous to a contiguous RNA sequence in an mRNA of myosin II or the like, and an antisense RNA chain consisting of a sequence complementary to the sense RNA sequence. The manufacturing and designing of the siRNA and mutant siRNA described below are within the scope of the ability of those skilled in the art. The concept of selecting any contiguous RNA region of an mRNA, which is a transcription product of a sequence of myosin II or the like, and creating a double-stranded RNA corresponding to the region is a matter within the normal creative ability of those skilled in the art. Further, a siRNA sequence with a more potent RNAi effect can be appropriately selected by those skilled in the art from an mRNA sequence, which is a transcription product of the sequence, using a known method. Further, if one of the strands is identified, those skilled in the art can readily determine the base sequence of the other strand (complementary strand). Those skilled in the art can appropriately create a siRNA using a commercially available nucleic acid synthesizer. Further, a common synthesis service can be utilized for synthesis of a desired RNA.

The length of a double-stranded RNA moiety, as a base, is 15 to 40 bases, preferably 15 to 30 bases, more preferably 15 to 25 bases, still more preferably 18 to 23 bases, and most preferably 19 to 21 bases. It is understood that the upper and lower limits thereof are not limited to the specified limits, where the limits can be any combinations of the mentioned limits. The terminal structure of a sense strand or antisense strand of a siRNA is not particular limited, which can be appropriately selected depending on the objective. For example, the terminal structure may have a smooth terminal or a protruding terminal (overhang), while a protruding 3' terminal is preferable. A siRNA having an overhang consisting of several bases, preferably 1 to 3 bases, and still more preferably 2 bases at the 3' terminal of a sense RNA strand and antisense RNA strand is preferred for often having a large effect of suppressing the expression of a target gene. The overhang base type is not particularly limited, which can be either a base constituting an RNA or a base constituting a DNA. Preferable overhang sequences include dTdT (2 bp of deoxy T) at the 3' terminal and the like. Examples of preferred siRNAs include, but are not limited to, those with dTdT (2 bp of deoxy T) added to the 3' terminal of sense and antisense strands of all siRNAs.

Furthermore, it is also possible to use a siRNA in which one to several nucleotides are deleted, substituted, inserted and/or added in either or both of the sense strand and antisense strand of the above-described siRNA. In this regard, the concept of one to several bases is not particularly limited, but is preferably 1 to 4 bases, still more preferably 1 to 3 bases, and most preferably 1 to 2 bases. Specific examples of such a mutation include, but are not limited to, mutations in which the number of bases at the 3' overhang moiety is from 0 to 3, mutations in which the base sequence of the 3'-overhang moiety is changed to another base sequence, mutations in which the lengths of the above-described sense RNA strand and antisense RNA strand are different by 1 to 3 bases due to an insertion, addition or deletion of bases, mutations in which the base in a sense strand and/or antisense strand is substituted with another base, and the like. However, it is necessary for the sense strand and the antisense strand to be able to hybridize in such mutant siRNAs, and for such mutant siRNAs to have the same ability to suppress gene expression as a siRNA that does not have a mutation.

Furthermore, a siRNA may be a molecule in which one end has a closed structure, such as a siRNA with a hairpin structure (Short Hairpin RNA; shRNA). A shRNA is an RNA comprising a sense strand RNA of a specific sequence of a target gene, an antisense strand RNA consisting of a sequence complementary to the sense strand sequence, and a linker sequence connecting the two strands, wherein the sense strand moiety and the antisense strand moiety hybridize to form a double-stranded RNA moiety It is desirable that a siRNA does not exhibit the so-called off-target effect in clinical use. An off-target effect refers to an effect of suppressing the expression of another gene partially homologous to the siRNA used, other than the target gene. It is possible to confirm that a candidate siRNA does not have cross reactivity by using a DNA microarray or the like in advance in order to avoid an off-target effect. Further, it is possible to avoid an off-target effect by confirming whether there is a gene comprising a moiety that is highly homologous to a sequence of a candidate siRNA, other than a target gene, by using a known database provided by the NCBI (National Center for Biotechnology Information) or the like.

In order to create the siRNA according to the present invention, a known method, such as a method using chemical synthesis or a method using a gene recombination technique, can be appropriately used. With a method using synthesis, a double-stranded RNA can be synthesized based on sequence information by using a common method. With a method using a gene recombination technique, a siRNA can be made by constructing an expression vector encoding a sense strand sequence or an antisense strand sequence and introducing the vector into a host cell, and then obtaining each of sense strand RNA and antisense strand RNA produced by transcription. Further, it is possible to create a desired double-stranded RNA by expressing a shRNA forming a hairpin structure, which comprises a sense strand of a specific sequence of a target gene, an antisense strand consisting of a sequence complementary to the sense strand sequence, and a linker sequence for linking the two strands.

For a siRNA, all or part of the nucleic acid constituting the siRNA may be a natural or a modified nucleic acid as long as such a nucleic acid has an activity to suppress the expression of a target gene.

The siRNA according to the present invention is not necessarily a pair of double-stranded RNAs to a target sequence. It may be a mixture of a plurality of pairs (the "plurality" is not particularly limited, but preferably refers to a small number of about 2 to 5) of double-stranded RNAs to a region comprising a target sequence. In this regard, those skilled in the art can appropriately create a siRNA as a nucleic acid mixture corresponding to a target sequence by using a commercially available nucleic acid synthesizer and a DICER enzyme. Further, a common synthesis service can be utilized for synthesis of a desired RNA. It should be noted that the siRNA according to the present invention encompasses the so-called "cocktail siRNA". For the siRNA according to the present invention, not all of the nucleotides have to be a ribonucleotide (RNA). Specifically, in the present invention, one or plurality of ribonucleotides constituting a siRNA may be a corresponding deoxyribonucleotide. The term "corresponding" refers to having the same base type (adenine, guanine, cytosine, thymine (uracil)) but a different sugar moiety structure. For example, a deoxyribonucleotide corresponding to a ribonucleotide having adenine refers to a deoxyribonucleotide having adenine.

Furthermore, a DNA (vector) which can express the above-described RNA according to the present invention is also encompassed as a preferred embodiment of a nucleic acid which can suppress expression of myosin II or the like. For example, the DNA (vector) which can express the above-described double-stranded RNA according to the present invention is a DNA having a structure in which a DNA encoding one of the strands of the double-stranded RNA and a DNA encoding the other strand of the double-stranded RNA are linked with a promoter so that each of the DNAs can be expressed. The above-described DNA according to the present invention can be appropriately made by those skilled in the art by using a common genetic engineering technique. More specifically, the expression vector according to the present invention can be made by appropriately inserting the DNA encoding an RNA according to the present invention into various known expression vectors.

In the present invention, a modified nucleic acid may be used as a nucleic acid for suppressing the expression of a target gene. A modified nucleic acid refers to a nucleic acid, which has a modification at a nucleoside (base moiety, sugar moiety) and/or an inter-nucleoside binding site, and has a structure different from that of a natural nucleic acid. Examples of "modified nucleoside", which constitutes a modified nucleic acid, include: an abasic nucleoside; arabinonucleoside, 2'-deoxyuridine, α-deoxyribonucleoside, β-L-deoxyribonucleoside, and nucleoside having other sugar modification; peptide nucleic acid (PNA), phosphate group-binding peptide nucleic acid (PHONA), locked nucleic acid (LNA), morpholino nucleic acid and the like. The above-described nucleosides having a sugar modification include 2'-O-methylribose, 2'-deoxy-2'-fluororibose, 3'-O-methylribose and other substituted pentose; 1',2'-deoxyribose; arabinose; substituted arabinose sugar; and nucleoside having a sugar modification of alpha-anomer and hexose. These nucleosides may be a modified base in which the base moiety is modified. Examples of such modified bases include 5-hydroxycytosine, 5-fluorouracil, 4-thiouracil and other pyrimidine; 6-methyladenine, 6-thioguanosine and other purine; other heterocyclic bases and the like.

Examples of a "modified inter-nucleoside bond", which constitutes a modified nucleic acid, include alkyl linker, glyceryl linker, amino linker, poly(ethylene glycol) bond, inter-methyl phosphonate nucleoside bond; and non-natural inter-nucleoside bonds of methylphosphonothioate, phosphotriester, phosphothiotriester, phosphorothioate, phosphorodithioate, triester prodrug, sulfone, sulfonamide, sulfamate, formacetal, N-methylhydroxylamine, carbonate, carbamate, morpholino, boranophosphonate, phosphoramidate and the like.

The nucleic acid sequence comprised in the double-stranded siRNA according to the present invention includes a siRNA directed to myosin II or other myosin II signaling members, and the like.

It is also possible to introduce the nucleic acid or agent according to the present invention into a phospholipid endoplasmic reticulum such as a liposome and to administer the endoplasmic reticulum. An endoplasmic reticulum in which a siRNA or shRNA is retained can be introduced into a predetermined cell (e.g., corneal endothelial cell) using lipofection. The resulting cell is then systemically-administered, for example intravenously, intra-arterially or the like. The endoplasmic reticulum can also be locally administered to a required site in an eye or the like. While a siRNA exhibits a very good specific, post-transcription suppressing effect in vitro, the siRNA is quickly degraded in vivo due to nuclease activity in the serum. Since the duration thereof is limited, there has been a need for development of a better and more effective delivery system. As an example, OCHIYA, T et al., Nature Med., 5: 707-710, 1999, Curr. Gene Ther., 1: 31-52, 2001 reports that a biocompatible material atelocollagen, when mixed with a nucleic acid to form a complex, is a carrier having an action of protecting a nucleic acid from a degrading enzyme in a living organism and is extremely suitable as a carrier of a siRNA. While such a form can be used, the method for introducing a nucleic acid or medicament according to the present invention is not limited to this method. In this manner, due to fast degradation by the action of a nucleic acid degrading enzyme in serum in a living organism, continued effect for an extended period of time can be achieved. For example, Takeshita F. PNAS, (2003) 102 (34) 12177-82, Minakuchi Y Nucleic Acids Research (2004) 32 (13) e109 reports that atelocollagen derived from bovine skin forms a complex with a nucleic acid, which has action of protecting a nucleic acid from a degrading enzyme in a living organism and is very suitable as a carrier of a siRNA. Such a technique can be used.

As used herein, "agent" is used in a broad sense, and may refer to any substance or other elements (e.g., energy such as light, radiation, heat, and electricity) as long as the intended objective can be attained. Examples of such a substance include, but are not limited to, proteins, polypeptides, oligopeptides, peptides, polynucleotides, oligonucleotides, nucleotides, nucleic acids (e.g., including DNAs such as cDNA and genomic DNA, and RNAs such as mRNA), polysaccharides, oligosaccharides, fats, organic small molecules (e.g., hormones, ligands, information transmitting substances, organic small molecules, molecules synthesized by combinatorial chemistry, small molecules which can be utilized as a medicine (e.g., a low molecular weight ligand) and the like), and composite molecule thereof. Representative examples of an agent specific to a polynucleotide include, but are not limited to, a polynucleotide having complementarity with certain sequence homology (e.g., 70% or more sequence identity) relative to the sequence of the polynucleotide, a polypeptide such as a transcription factor binding to a promoter region, and the like. Representative examples of an agent specific to a polypeptide include, but are not limited to, an antibody specifically directed to the polypeptide or a derivative or an analogue thereof (e.g., single-stranded antibody), a specific ligand or receptor when the polypeptide is a receptor or a ligand, a substrate when the polypeptide is an enzyme, and the like.

As used herein, "disease, disorder or condition of corneal endothelium" refers to any disease, disorder or condition of the corneal endothelium, especially those associated with myosin II. Examples thereof include Fuchs' endothelial corneal dystrophy, corneal endotheliitis, trauma, ophthalmic surgery and the like. Such a disorder includes, but is not limited to, photophobia, blurred vision, visual impairment, ophthalmalgia, epiphora, hyperemia, pain, bullous keratopathy, eye discomfort, diminished contrast, glare, edema of the corneal stroma, corneal turbidity and the like.

As used herein, "corneal endothelial cell" is used in the general sense used in the art. A cornea is one of the lamellar tissues constituting an eye. A cornea is transparent and is positioned at a part closest to the external environment. In humans, it is understood that the cornea is composed of five layers, corneal epithelium, Bowman's membrane (external boundary), Lamina propria, Descemet's membrane (internal boundary), and corneal endothelium, in order, from the outside (body surface). Unless specifically noted otherwise, parts other than the epithelium and endothelium may be collectively called "corneal stroma", which is also called as such herein.

As used herein, any corneal endothelial cell can be used as the "corneal endothelial cell". Primary culture cells can naturally be used, as well as subcultured or grown cells, cells induced to differentiate from undifferentiated cells such as stem cells (ES cells, iPS cells or the like) or the like. As used herein, "HCEC" (human corneal endothelial cells) is an abbreviation for human corneal endothelial cells. In addition, "iHCEC" is an abbreviation for immobilized human corneal endothelial cells. Corneal endothelial cells prepared from normal corneal endothelial cells by using the approach described in WO 2013/100208, which is a previous technique of the Applicant, but the corneal endothelial cells are not limited thereof.

As used herein, "undifferentiated cells" refers to any cell with the ability to differentiate. Thus, undifferentiated cells encompass stem cells, as well as cells that are differentiated to a certain level but can further differentiate.

As used herein, "isolated" refers to a state where a substance that naturally accompanies an object or interest under normal environment is at least reduced, preferably a state where an object or interest is substantially free of such a substance. Thus, isolated cells, tissue or the like refer to cells that are substantially free of other accompanying substances (e.g., other cells, proteins, nucleic acids or the like) in a natural environment. Isolated corneal endothelial cells can be used in the present invention.

As used herein, "normal cell function" of cells refers to a function inherent in the cells when referring to specific cells such as corneal endothelial cells. Examples of such a function for corneal endothelial cells include, but are not limited to, adaptability to ZO-1, $Na^+/K^+$-ATPase and corneal transplantation (Matsubara M, Tanishima T: Wound-healing of the corneal endothelium in the monkey: a morphometric study, Jpn J Ophthalmol 1982, 26: 264-273; Matsubara M, Tanishima T: Wound-healing of corneal endothelium in monkey: an autoradiographic study, Jpn J Ophthalmol 1983, 27: 444-450; Van Horn D L, Hyndiuk R A: Endothelial wound repair in primate cornea, Exp Eye Res 1975, 21: 113-124 and Van Horn D L, Sendele D D, Seideman S, Buco P J: Regenerative capacity of the corneal endothelium in rabbit and cat, Invest Ophthalmol Vis Sci 1977, 16: 597-613). In the present invention, it is preferable to use corneal endothelial cells confirmed to have a normal cell function.

ZO-1 and Na⁺/K⁺-ATPase can be assessed by observing gene expression by immunological means or by observing the expression at nucleic acid levels in RT-PCR or the like. Na⁺/K⁺-ATPase and ZO-1 can be verified to be expressed and/or functioning at the same level as normal cells to examine whether the cells of interest has a normal function.

(General Techniques)

Molecular biological approach, biochemical approach, microbiological approach used herein are well known and conventionally used in the art, which are described for example in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [*Experimental Medicine, Supplemental Volume*], Idenshi Donyu & Hatsugen Kaiseki Jikken Ho [*Experimental Methods for Transgenesis & Expression Analysis*], Yodosha, 1997, or the like. The reports by Nancy Joyce et al {Joyce, 2004 #161} and {Joyce, 2003 #7} are well known for corneal endothelial cells. However, as discussed above, long-term culture or subculture results in fibroblast-like transformation, and research for an effective culturing method is currently ongoing. Relevant portions thereof (which may be the entire document) are incorporated herein by reference.

Description of Preferred Embodiments

Preferred embodiments of the present invention are described below. It is understood that the embodiments are exemplification of the present invention, and as such, the scope of the present invention is not limited to such preferred embodiments. It should be understood that those skilled in the art can readily make modifications or changes within the scope of the present invention while referring to the following preferred examples. For such embodiments, those skilled in the art can appropriately combine any embodiments.

(Treatment or Prevention of Disease, Disorder or Condition of Corneal Endothelium, Comprising Myosin II-Specific Inhibitor)

In one aspect, the present invention provides a medicament for treating or preventing a disease, disorder or condition of a corneal endothelium, comprising a myosin II-specific inhibitor. It was discovered in the present invention that administration of a myosin II-specific inhibitor unexpectedly improved, prevented, or healed a corneal endothelial disease, disorder or condition. Thus, such an application of a myosin II-specific inhibitor to treat or prevent a disease, disorder or condition of a corneal endothelium is recognized as unexpected from conventional knowledge.

In a preferred aspect, the present invention provides a medicament for treating or preventing a diseases, disorder or condition of a corneal endothelium, comprising a corneal endothelial cell and a myosin II-specific inhibitor. The effect of the myosin II-specific inhibitor is notably exhibited when the corneal endothelial cell is externally applied. Although not wishing to be bound by any theory, this is considered to promote establishment of corneal endothelial cells to a cornea.

In a preferred embodiment, the disease, disorder or condition targeted by the present invention is a disorder related to bullous keratopathy. There is currently no fundamental therapeutic method of technique for bullous keratopathy. Thus, therapy for bullous keratopathy must rely on corneal transplantation. Since the present invention can notably treat or prevent bullous keratopathy, it is understood to be useful in treating or preventing bullous keratopathy.

In one specific embodiment, the disease, disorder or condition targeted by the present invention includes, but is not limited to, photophobia, blurred vision, visual impairment, ophthalmalgia, epiphora, hyperemia, pain, eye discomfort, diminished contrast, glare, edema of the corneal stroma, corneal turbidity and the like in bullous keratopathy.

Targets of administration (transplantation) of the therapeutic or prophylactic drug or method of the present invention include mammals (e.g., humans, mice, rats, hamsters, rabbits, cats, dogs, cows, horses, sheep, monkeys and the like). However, primates are preferred and humans are especially preferred. Satisfactory results have not been attained by corneal endothelial therapy in primates up to this point. In view of the above, the present invention provides an innovative therapeutic method and medicament.

Any agent may be used as the myosin II-specific inhibitor used in the present invention, as long as myosin II can be inhibited. Further, myosin II specific pathways to be inhibited may be directly associated with a myosin II chain (heavy chain or light chain) as is well known, and any factor associated with a signal may be used as long as it ultimately exerts the same (opposite for inhibitor/antagonist etc.) effect as a myosin II signaling pathway. Particularly in the examples, an effect is exerted by using an agent for inhibiting phosphorylation of a myosin light chain (MLC). Thus, such an agent inhibiting phosphorylation of MLC can be preferably used, but is not limited thereto.

The present invention can also include a myosin II-specific inhibitor alone or in combination of several types as needed.

In one embodiment, a myosin II-specific inhibitor comprises at least one type of myosin II antagonist, myosin II subunit phosphorylation inhibitor, especially phosphorylation inhibitor of MLC, myosin light chain kinase inhibitor, other ingredients exemplified herein, pharmaceutically acceptable salt or solvent thereof, or solvate of a pharmaceutically acceptable salt thereof. Any substance described in other parts of the present specification can be used as each of such ingredients.

A myosin II-specific inhibitor which can be used in the present invention comprises at least one type of blebbistatin, myosin II-specific antibody, myosin II-specific siRNA, peptide aptamer, shRNA, decoy, antisense, other ingredients exemplified herein, pharmaceutically acceptable salt or solvent thereof, or solvate of a pharmaceutically acceptable salt thereof. The mentioned antibodies may be a neutralizing antibody, but are not limited thereto.

In a preferred embodiment, the myosin II-specific inhibitor which is used in the present invention comprises blebbistatin ((S)-(−)-Blebbistatin; CAS No: 856925-71-8; Reference document; Straight, A. F., et al.: Science, 299, 1743 (2003)). This is because it was shown that a disease, disorder or condition associated with extracellular matrix (ECM) abnormality in a corneal endothelium such as Fuchs' endothelial corneal dystrophy is ameliorated. In a preferred embodiment, blebbistatin is comprised to be present at a concentration of about 0.1 μM to about 10 μM in use, preferably at a concentration of about 1 μM to about 10 μM in use, and still more preferably at a concentration of about 1 μM in use.

The concentration of the myosin II-specific inhibitor used in the present invention is generally about 0.1 to 100 μmol/l, preferably about 0.1 to 30 μmol/l, and more preferably about 1 μmol/l. When several types thereof are used, the concentration may be changed appropriately. Examples of other concentration ranges include, but not limited to, generally about 0.001 to 100 μmol/l, preferably about 0.01 to 75 μmol/l, about 0.05 to 50 μmol/l, about 1 to 10 μmol/l, about 0.01 to 10 μmol/l, about 0.05 to 10 μmol/l, about 0.075 to 10 μmol/l, about 0.1 to 10 μmol/l, about 0.5 to 10 μmol/l, about 0.75 to 10 μmol/l, about 1.0 to 10 μmol/l, about 1.25 to 10 μmol/l, about 1.5 to 10 μmol/l, about 1.75 to 10 μmol/l, about 2.0 to 10 μmol/l, about 2.5 to 10 μmol/l, about 3.0 to 10 μmol/l, about 4.0 to 10 μmol/l, about 5.0 to 10 μmol/l, about 6.0 to 10 μmol/l, about 7.0 to 10 μmol/l, about 8.0 to 10 μmol/l, about 9.0 to 10 μmol/l, about 0.01 to 50 μmol/l, about 0.05 to 5.0 μmol/l, about 0.075 to 5.0 μmol/l, about 0.1 to 5.0 μmol/l, about 0.5 to 5.0 μmol/l, about 0.75 to 5.0 μmol/l, about 1.0 to 5.0 μmol/l, about 1.25 to 5.0 μmol/l, about 1.5 to 5.0 μmol/l, about 1.75 to 5.0 μmol/l, about 2.0 to 5.0 μmol/l, about 2.5 to 5.0 μmol/l, about 3.0 to 5.0 μmol/l, about 4.0 to 5.0 μmol/l, about 0.01 to 3.0 μmol/l, about 0.05 to 3.0 μmol/l, about 0.075 to 3.0 μmol/l, about 0.1 to 3.0 μmol/l, about 0.5 to 3.0 μmol/l, about 0.75 to 3.0 μmol/l, about 1.0 to 3.0 μmol/l, about 1.25 to 3.0 μmol/l, about 1.5 to 3.0 μmol/l, about 1.75 to 3.0 μmol/l, about 2.0 to 3.0 μmol/l, about 0.01 to 1.0 μmol/l, about 0.05 to 1.0 μmol/l, about 0.075 to 1.0 μmol/l, about 0.1 to 1.0 μmol/l, about 0.5 to 1.0 μmol/l, about 0.75 to 1.0 μmol/l, about 0.09 to 35 μmol/l, about 0.09 to 3.2 μmol/l, and more preferably about 0.05 to 1.0 μmol/l, about 0.075 to 1.0 μmol/l, about 0.1 to 1.0 μmol/l, about 0.5 to 1.0 μmol/l, and about 0.75 to 1.0 μmol/l.

The medicament of the treatment or prevention of the present invention may comprise an additional pharmaceutical ingredient. Representative examples of such a pharmaceutical product include RhoA inhibitors, Rho kinase inhibitors, steroids and the like. Although not wishing to be bound by any theory, this is because the effect of a myosin II-specific inhibitor can be enhanced, since inclusion of a RhoA inhibitor and/or a Rho kinase inhibitor and/or a steroid allows prevention of cell loss by promoting adhesion of corneal endothelial cells and formation of a corneal endothelial cell layer with excellent cell morphology and high cellular density. The present invention can comprise one type of RhoA inhibitor and/or Rho kinase inhibitor alone or several types thereof for combined use as needed.

At least one type of botulinum C3 enzyme (C3), RhoA specific antibody, RhoA specific siRNA, peptide aptamer, shRNA, decoy, antisense, other ingredients exemplified herein, pharmaceutically acceptable salt or solvent thereof, and solvate of a pharmaceutically acceptable salt thereof is comprised as a Rho kinase inhibitor that can be used in the present invention. The mentioned antibodies may be a neutralizing antibody, but are not limited thereto.

At least one type of compounds disclosed in the following documents: U.S. Pat. No. 4,678,783, Japanese Patent No. 3421217, International Publication No. WO 95/28387, International Publication No. WO 99/20620, International Publication No. WO 99/61403, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, International Publication No. WO 2007/026664 and the like; Rho kinase specific antibodies; Rho kinase specific siRNAs; peptide aptamers; shRNAs decoys; antisenses; other ingredients exemplified herein; pharmaceutically acceptable salts or solvents thereof; and solvates of a pharmaceutically acceptable salt thereof is comprised as a Rho kinase inhibitor that can be used in the present invention. The mentioned antibodies may be a neutralizing antibody, but are not limited thereto. Each of such compounds can be manufactured by the methods described in the documents in which the respective compounds are disclosed. Examples thereof include 1-(5-isoquinolinesulfonyl)homopiperazine or a salt thereof (e.g., fasudil (1-(5-isoquinolinesulfonyl)homopiperazine)), (R)-(+)-trans-(4-pyridyl)-4-(1-aminoethyl)-cyclohexanecarboxamide) or a salt thereof (e.g., Y-27632 ((R)-(+)-trans-(4-pyridyl)-4-(1-aminoethyl)-dihydrochloride cyclohexanecarboxamide monohydrate) and the like) and the like.

The concentration of the RhoA inhibitor, Rho kinase inhibitor, or steroid in the present invention is generally about 1 to 100 μmol/l, preferably about 5 to 20 μmol/l, and more preferably about 10 μmol/l. When several types thereof are used, the concentration may be changed appropriately. Examples of other concentration ranges include, but are not limited to, generally about 0.001 to 100 μmol/l, preferably about 0.01 to 75 μmol/l, about 0.05 to 50 μmol/l, about 1 to 10 μmol/l, about 0.01 to 10 μmol/l, about 0.05 to 10 μmol/l, about 0.075 to 10 μmol/l, about 0.1 to 10 μmol/l, about 0.5 to 10 μmol/l, about 0.75 to 10 μmol/l, about 1.0 to 10 μmol/l, about 1.25 to 10 μmol/l, about 1.5 to 10 μmol/l, about 1.75 to 10 μmol/l, about 2.0 to 10 μmol/l, about 2.5 to 10 μmol/l, about 3.0 to 10 μmol/l, about 4.0 to 10 μmol/l, about 5.0 to 10 μmol/l, about 6.0 to 10 μmol/l, about 7.0 to 10 μmol/l, about 8.0 to 10 μmol/l, about 9.0 to 10 μmol/l, about 0.01 to 50 μmol/l, about 0.05 to 5.0 μmol/l, about 0.075 to 5.0 μmol/l, about 0.1 to 5.0 μmol/l, about 0.5 to 5.0 μmol/l, about 0.75 to 5.0 μmol/l, about 1.0 to 5.0 μmol/l, about 1.25 to 5.0 μmol/l, about 1.5 to 5.0 μmol/l, about 1.75 to 5.0 μmol/l, about 2.0 to 5.0 μmol/l, about 2.5 to 5.0 μmol/l, about 3.0 to 5.0 μmol/l, about 4.0 to 5.0 μmol/l, about 0.01 to 3.0 μmol/l, about 0.05 to 3.0 μmol/l, about 0.075 to 3.0 μmol/l, about 0.1 to 3.0 μmol/l, about 0.5 to 3.0 μmol/l, about 0.75 to 3.0 μmol/l, about 1.0 to 3.0 μmol/l, about 1.25 to 3.0 μmol/l, about 1.5 to 3.0 μmol/l, about 1.75 to 3.0 μmol/l, about 2.0 to 3.0 μmol/l, about 0.01 to 1.0 μmol/l, about 0.05 to 1.0 μmol/l, about 0.075 to 1.0 μmol/l, about 0.1 to 1.0 μmol/l, about 0.5 to 1.0 μmol/l, about 0.75 to 1.0 μmol/l, about 0.09 to 35 μmol/l, about 0.09 to 3.2 μmol/l, and more preferably about 0.05 to 1.0 μmol/l, about 0.075 to 1.0 μmol/l, about 0.1 to 1.0 μmol/l, about 0.5 to 1.0 μmol/l, and about 0.75 to 1.0 μmol/l.

The present invention can be administered as eye drops.

The dosage and dosing frequency vary depending on the symptom, age, weight, or mode of administration. For example, when used as eye drops, a formulation containing about 0.0001-0.1 w/v % of effective ingredient, preferably about 0.003-0.03 w/v % can generally be administered 1-10 times a day, preferably 1-6 times, more preferably 1-3 times with about 0.01-0.1 mL per dose for adults. When the medicament of the treatment or prevention of the present invention is injected into the anterior chamber, a formulation with a concentration that is 1/10 to 1/1000 of the above-described concentration may be used. Those skilled in the art can appropriately select the type and concentration of myosin II-specific inhibitor, Rho kinase inhibitor or the like depending on the condition of the disease.

In one aspect, the present invention provides a corneal endothelial formulation comprising a myosin II-specific inhibitor and a corneal endothelial cell.

In one aspect, the corneal endothelial formulation of the present invention comprises a substrate and a corneal endothelial cell layer cultured in vitro on the substrate.

The substrate used in the present invention is not particularly limited, as long as the substrate can carry a cultured corneal endothelial cell layer and maintain the shape thereof in a living body for a certain period of time after transplantation, preferably at least three days. Further, the substrate used in the present invention may serve a role as a scaffold when corneal endothelial cells are cultured in a test tube. The substrate may also serve a role of only carrying a cultured corneal endothelial cell layer after culture. Preferably, the substrate used in the present invention is used in culturing corneal endothelial cells and serves a role as a scaffold capable of being subjected to transplantation directly after completion of culture.

Examples of the substrate used in the present invention include collagen, gelatin, cellulose and other naturally-derived polymeric materials, polystyrene, polyester, polycarbonate, poly(N-isopropylacrylamide) and other synthetic polymeric materials, polylactate, polyglycolic acid and other biodegradable polymeric materials, hydroxyapatite, amnion and the like. The shape of the substrate used in the present invention is not particularly limited, as long as it is a shape that can carry a corneal endothelial cell layer and is suitable for transplantation. However, a sheet-like shape is preferred. When the formulation of the present invention has a sheet-like shape, it is possible to cut the formulation into a size matching the site of application upon transplantation. Further, it is also possible to insert the sheet, after rolling the sheet up into a smaller size, from an open wound. A specific preferred example includes a circular shape covering about 80% of the area of damaged corneal endothelium. Further, it is preferred that a notch is provided at the periphery of the circular shape such that the substrate can adhere to the applied site.

In a preferred embodiment, an example of a substrate used in the present invention is collagen. The collagen sheet described in Japanese Laid-Open Publication No. 2004-24852 can be suitably used as the collagen. The collagen sheet can be prepared, for example, from amnion in accordance with the method described in Japanese Laid-Open Publication No. 2004-24852.

Hereinafter, preparation of a corneal endothelial cell layer is described as an example of a corneal endothelial formulation.

The corneal endothelial cell layer used in the present invention preferably comprises at least one of the following features, more preferably two or more of the following features, and still more preferably all of the following features.

(1) A cell layer has a single layer structure. This is one of the features a corneal endothelial cell layer in a living body has.
(2) The cell density in the cell layer is about 1000-4000 cells/mm$^2$. Preferably, the cell density is about 2000-3000 cells/mm$^2$ especially when the recipient is an adult.
(3) The shape of constituent cells of the cell layer is approximately a hexagon in plan view. This is one of the features constituent cells of a corneal endothelial cell layer in a living body have. The formulation of the present invention is similar to a corneal endothelial cell layer in a living body. The formulation exerts the same function as a native corneal endothelial cell layer and can exhibit an ability to grow in a living body.
(4) Cells are aligned orderly in a cell layer. Constituent cells of a corneal endothelial cell layer in a living body are aligned orderly. It is conjectured that normal function and high transparency of corneal endothelial cells are maintained, and moisture regulating function of the cornea is suitably exerted thereby. Thus, the formulation of the present invention is expected to exert the same function as a corneal endothelial cell layer in a living body by comprising such morphological features.

The corneal endothelial cells used in the present invention can be collected and cultured in a test tube as follows.

Corneal endothelial cells are collected by a conventional method from the recipient's own cornea or a suitable donor's cornea. Considering the transplantation conditions in the present invention, it is sufficient to prepare allogenic corneal endothelial cells. For example, the Descemet's membrane and endothelial cell layer of corneal tissue are detached from the corneal stroma and then transferred to a culture dish for treatment with Dispase. The corneal endothelial cells fall off from the Descemet's membrane thereby. The corneal endothelial cells remaining on the Descemet's membrane can be made to fall off by pipetting. After removing the Descemet's membrane, the corneal endothelial cells are cultured in a suitable culture solution. It is possible to use, as a suitable culture solution, a commercially available DMEM (Dulbecco's Modified Eagle's Medium) (e.g., INVITROGEN, catalog number: 12320 or the like), to which FBS (fetal bovine serum) (e.g., BIO-WEST, catalog number: S1820-500), b-FGF (basic fibroblast growth factor) (e.g., INVITROGEN, catalog number: 13256-029) and an antibiotic such as penicillin or streptomycin are appropriately added, as well as a component of a culture normalizing agent (typical example includes, but is not limited to, SB431542 (4-[4-(1,3-benzodioxole-5-yl)-5-(2-pyridinyl)]-1H-imidazole-2-yl]benzamide). For details WO 2013/100208 can be referred) such as a fibrosis inhibitor such as a transforming growth factor (TGF) β signal inhibitor. It is preferable to use a culture container (culture dish) whose surface is coated with type I collage, type IV collagen, fibronectin, laminin or extracellular matrix of a bovine corneal endothelial cell. Alternatively, a common culture container may be used, which is treated with a commercially available coating agent such as FNC coating Mix® (50 ml (AES-0407), ATHENA, catalog numbering number: 0407). This is because combined use of said coating and a suitable culture solution promotes adhesion of corneal endothelial cells to the surface of a culture container for excellent growth.

The temperature conditions for culturing corneal endothelial cells are not particularly limited, as long as corneal endothelial cells can grow. For example, the temperature is about 25° C. to about 45° C. Considering the growth efficiency, the temperature is preferably about 30° C. to about 40° C. and more preferably about 37° C. A culturing method is implemented under humid condition in an environment of about 5-10% $CO_2$ concentration in a common cell culture incubator.

After the growth of corneal endothelial cells subjected to culturing, subculture can be carried out. Subculture is preferably carried out when the cells are sub-confluent or when the cells have reached confluence. Subculture is carried out as follows. First, cells are peeled off from the surface of a culture container by treating the cells with trypsin-EDTA or the like, and then the cells are collected. The aforementioned culture normalizing agent or medium is added to the collected cells to make a cell suspension. It is preferable that the suspension is centrifuged when cells are collected or after the cells are collected. Centrifugation allows preparation of a cell suspension with a high cell density. Preferred cell density is about 1 to $2 \times 10^6$ cells/mL. Examples of centrifugation conditions include 500 rpm (30×g) to 1000 rpm (70×g), and 1 to 10 minutes.

A cell suspension is seeded in a culture container in the same manner as the above-described primary culture and subjected to culturing. The dilution factor for subculture, although dependent on the cell condition, is about 1:2-1:4, preferably about 1:3. Subculture can be carried out under the same culture conditions as the above-described primary culture. The time of culture, although dependent on the condition of cells used, is for example 7 to 30 days. The subculture can be carried out multiple times as needed. If a cell adhesion promotor is used in the aforementioned culture normalizing agent or suitable culture solution, the period of culture can be shortened by elevating cell adhesion at the early stages of culture.

A corneal endothelial cell layer can be prepared as follows. A cell suspension is seeded on a substrate such as a collagen sheet and subjected to culture. For this culturing, the number of cells seeded is adjusted such that a cell layer with a desired cell density is formed in the corneal endothelial formulation ultimately manufactured. Specifically, cells are seeded such that a cell layer with a cell density of about 1000 to about 4000 cells/mm$^2$ is formed. Culture can be carried out under the same conditions as the above-described primary culture or the like. The time of culture, although dependent on the condition of cells used, is for example 3 to 30 days.

In this manner, culturing results in a corneal endothelial formulation in which a corneal endothelial cell layer cultured in a test tube is formed on a substrate.

Such a corneal endothelial formulation can be used as a graft in therapy of a disease requiring transplantation of a corneal endothelium, such as bullous keratopathy, corneal edema, corneal leukoma, especially bullous keratopathy caused by corneal endothelial disorder due to trauma or intraocular surgery or corneal dystrophy. Examples of a cause for such bullous keratopathy, corneal endothelial disorder or the like includes surgery as well as Fuchs' endothelial corneal dystrophy, pseudoexfoliation syndrome, corneal endotheliitis and the like.

In another aspect, the present invention provides a myosin II-specific inhibiting substance for improving, healing, treating, or preventing a disease, disorder, or condition of a corneal endothelium. A myosin II-specific inhibiting substance can be used interchangeably with a myosin II-specific inhibitor. In application, any embodiment described herein can be used for the disease, disorder or condition of a corneal endothelium and myosin II-specific inhibitor.

In another aspect, the present invention provides a method for improving, healing, treating, or preventing a disease, disorder or condition in a corneal endothelium in a subject, the method comprising administering an effective amount of myosin II-specific inhibitor to the subject. Any embodiment described herein can be used for the disease, disorder or condition of a corneal endothelium and myosin II-specific inhibitor in this method.

Targets of administration (transplantation) of the medicament of the treatment or prevention or method of the present invention include mammals (e.g., humans, mice, rats, hamsters, rabbits, cats, dogs, cows, horses, sheep, monkeys and the like). However, primates are preferred and humans are especially preferred. Satisfactory results have not been attained by corneal endothelial therapy in primates up to this point. In view of the above, the present invention provides an innovative therapeutic method and medicament.

Reference literatures such as scientific literatures, patents, and patent applications cited herein are incorporated herein by reference to the same extent that the entirety of each document is specifically described.

As described above, the present invention has been described by showing preferred embodiments to facilitate understanding. The present invention is described below based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

Reference Example 1

Examination of Cell Adhesion Due to ROCK Inhibitor and Effect Thereof on Adhesion-Related Molecule Reference Example 1 added a ROCK inhibitor to study the effect on cell adhesion due to inhibiting the Rho-ROCK pathway.

(Materials and Methods)
(Corneal Tissue)

All monkey corneal tissues used in this experiment were corneas of a cynomolgus monkey euthanized for other research purposes (Nissei Bilis Co., Ltd., Ohtsu, Japan, or Keari Co., Ltd., Wakayama, Japan). All corneas were preserved at 4° C. in a preservation medium (Optisol; Chiron Vision Corporation, Irvine, Calif.).

(Cell Culture)

In primary culture of monkey corneal endothelial cells, a Descemet's membrane including an endothelial cell layer was detached from a corneal tissue, and placed in 2 mg/ml Collagenase A (catalog No.: 70164923; Roche Applied Science, Penzberg, Germany) dissolved in DMEM (Gibco-Invitrogen) and incubated at 37° C. After 12 hours, the sample was centrifuged at 1000 rpm for 5 minutes to remove the supernatant. A culture medium was then added to a precipitated corneal endothelial cell mass for admixing. The entire amount was seeded on a 12-well plate coated with FNC Coating Mix (catalog No.: 0407; Athena Enzyme Systems, Baltimore, Md., USA). DMEM (catalog No.: 12320; Gibco-Invitrogen), to which 10% FBS, 50 µg/ml Gentamicin (catalog number: 15710-064; Invitrogen), and 2 ng/ml basic fibroblast growth factor, catalog number: 13256-029; bFGF; Invitrogen) were added, was used as a culture medium.

A medium was exchanged every other day. Subculture was performed when 50 to 80% confluence was reached. With respect to the subculturing method, cells were washed with $Ca^{2+}Mg^{2+}$-free PBS (PBS−; Nissui Pharmaceutical Co., Ltd., Tokyo, Japan), and TrypLE™ Select (catalog No.: 12563; Invitrogen) was added and incubated at 37° C. for 5 minutes. Cells were detached and collected from the plate. After the cells were centrifuged at 1000 rpm for 5 minutes, a culture medium was added to make a cell suspension. Cells were seeded on a plate coated with FNC Coating Mix at a density of 1:2-3.

(Examination of Number of Adhering Cells)

The number of adhering cells was analyzed by using CellTiter-Glo®. First, cultured monkey corneal endothelial cells were seeded on a 96 well plate at 5000 cells/well in a DMEM (Gibco-Invitrogen) to which Y-27632 (Wako, catalog number: 251-00514) was added such that the final concentration would be 10 µM. DMEM (Gibco-Invitrogen) was used as a control. The cells were washed with PBS(−) after three hours from seeding. PBS(−) was removed by tapping. The CellTiter-Glo® reagent and medium returned to room temperature were added thereto at 1:1 and shaken for 10 minutes in the dark. Furthermore, the mixture was left standing for 10 minutes for it to reach equilibrium. The mixture was then transferred to a white plate to measure absorbance.

(Western Blot)

DMEM (Gibco-Invitrogen) to which Y-27632 was added such that the final concentration would be 10 µM and cultured monkey corneal endothelial cells were seeded. Over time, i.e., 0, 1, 3, and 24 hours thereafter, proteins extracted with RIPA buffer were subjected to electrophoresis with 7.5% polyacrylamide. DMEM (Gibco-Invitrogen) was used as a control. The separated protein was transcribed onto a PVDF membrane (PALL LIFE SCIENCE, catalog number: EH-2222). Blocking procedure was carried out by incubating a Tris buffered saline (10 mM Tris-HCl, pH 7.4, 100 mM NaCl) supplemented with 0.1% (vol/vol) polyethylene sorbitan monolaurate (Nacalai Tesque, catalog number: 28353-85) (TBS-T) and 5% non-fat dry milk (CELL SIGNALING, catalog number: 9999) and the blotted membrane for one hour. The membrane was then immersed in TBS-T supplemented with antibodies against Phospho Myosin Light Chain 2 (Thr18/Ser19) (CELL SIGNALING, catalog number: 3674), Phospho FAK (Y397) (D20B1) Rabbit mAb (CELL SIGNALING, catalog number: 8556), Phospho Paxillin (Tyr118) Antibody (CELL SIGNALING, catalog number: 2541), GAPDH (14C10) Rabbit mAb (CELL SIGNALING, catalog number: 2118) and diluted 1000-fold, and reacted for 1 hour at room temperature. After washing three times with TBS-T, a mouse-IgG antibody HRP complex (CELL SIGNALING, catalog number: 7074P2) and rabbit-IgG antibody HRP complex (GE Healthcare, catalog number: NA934) were incubated, washed, and then made to emit light with ECL-ADVANCE (GE Healthcare Japan, catalog number: RPN2135V) to detect a band.

(Results)

The results are shown in FIG. 1. The left side of FIG. 1 is the result of examining cell adhesion due to a ROCK inhibitor by assessing the number of adhering cells with CellTiter-Glo®. It was found as a result that the number of adhering cells significantly increased when a ROCK inhibitor Y-27632 was added in comparison to the control.

The right side of FIG. 1 is a result of measuring the activity of adhesion-related molecules and Rho-ROCK pathway after the addition of a ROCK inhibitor by Western blot. It was possible to verify that the addition of Y-27632 suppresses MLC phosphorylation. Further, it was possible to verify that adhesion-related molecules FAK and paxillin are phosphorylated at an early stage.

Reference Example 2

Examination of Cell Adhesion Due to RhoA Inhibitor and Effect Thereof on Adhesion-Related Molecule Reference Example 2 used a RhoA inhibitor (botulinum C3 enzyme) to study the effect on cell adhesion.

(Materials and Methods)

In short, cell adhesion due to RhoA inhibitor was examined by assessing the number of adhering cells with CellTiter-Glo®. Further, the activity of adhesion-related molecules after the addition of a RhoA inhibitor was measured by Western blot.

(Examination of Number of Adhering Cells).

The number of adhering cells was analyzed by using CellTiter-Glo®. First, cultured monkey corneal endothelial cells were seeded onto a 96 well plate at 5000 cells/well in DMEM (Gibco-Invitrogen) to which C3 botulinum toxin (CALBIOCHEM, catalog number: 341208) was added such that the final concentration would be 300 ng/ml. DMEM (Gibco-Invitrogen) was used as a control. The cells were washed with PBS(−) after three hours from seeding. PBS(−) was removed by tapping. The CellTiter-Glo® reagent and medium returned to room temperature were added thereto at 1:1 and shaken for 10 minutes in the dark. Furthermore, the mixture was left standing for 10 minutes for it to reach equilibrium. The mixture was then transferred to a white plate to measure absorbance.

(Western Blot)

DMEM (Gibco-Invitrogen) to which C3 botulinum toxin was added such that the final concentration would be 300 ng/ml and cultured monkey corneal endothelial cells were seeded. Over time, i.e., 0, 1, 3, and 24 hours thereafter, proteins extracted with RIPA buffer were subjected to electrophoresis with 7.5% polyacrylamide. DMEM (Gibco-Invitrogen) was used as a control. The separated protein was transcribed onto a PVDF membrane (PALL LIFE SCIENCE, catalog number: EH-2222). Blocking procedure was carried out by incubating a Tris buffered saline (10 mM Tris-HCl, pH 7.4, 100 mM NaCl) supplemented with 0.1% (vol/vol) polyethylene sorbitan monolaurate (Nacalai Tesque, catalog number: 28353-85) (TBS-T) and 5% non-fat dry milk (CELL SIGNALING, catalog number: 9999) and the blotted membrane for one hour. The membrane was then immersed in TBS-T supplemented with antibodies against Phospho FAK (Y397) (D2051) Rabbit mAb (CELL SIGNALING, catalog number: 8556), Phospho Paxillin (Tyr118) Antibody (CELL SIGNALING, catalog number: 2541), GAPDH (14C10) Rabbit mAb (CELL SIGNALING, catalog number: 2118) and diluted 1000-fold, and reacted for 1 hour at room temperature. After washing three times with TBS-T, a mouse-IgG antibody HRP complex (CELL SIGNALING, catalog number: 7074P2) and rabbit-IgG antibody HRP complex (GE Healthcare, catalog number: NA934) were incubated, washed, and then made to emit light with ECL-ADVANCE (GE Healthcare Japan, catalog number: RPN2135V) to detect a band.

(Results)

Figure 2:
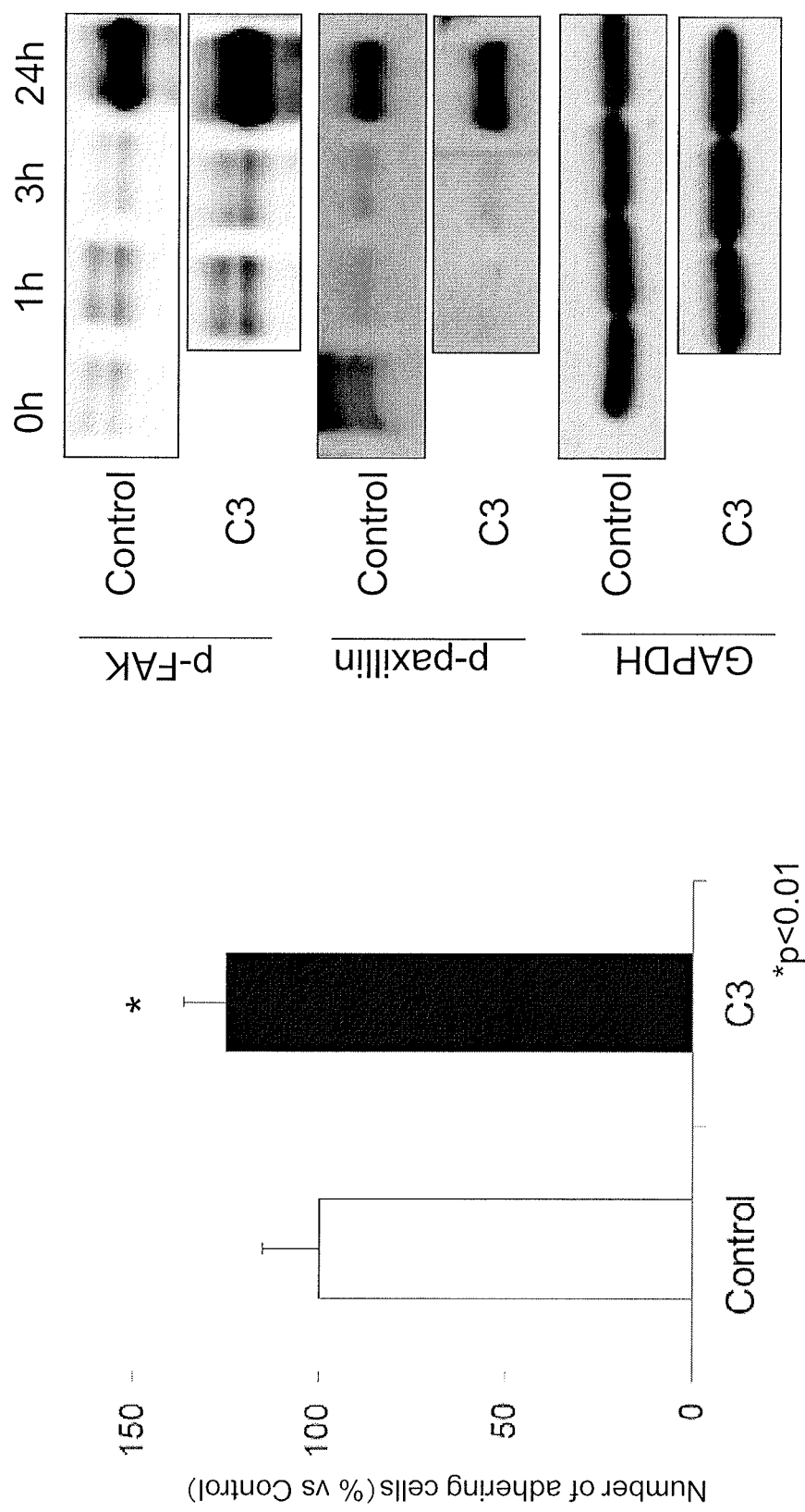
FIG. 2 shows the examination of cell adhesion due to an RhoA inhibitor and effect thereof on adhesion-related molecules. The effect on cell adhesion was investigated by using the action of an RhoA inhibitor (botulinum C3 enzyme). The left diagram shows results from examining cell adhesion due to an RhoA inhibitor by assessing the number of adhering cells with CellTiter-Glo®. It was found as a result that the number of adhering cells significantly increased when an RhoA inhibitor C3 was added in comparison to the control. The right diagram shows results of measuring the activity of adhesion-related molecules after the addition of an RhoA inhibitor by Western blot. It was possible to verify that the addition of a RhoA inhibitor C3 promotes phosphorylation of adhesion-related molecules FAK and paxillin.

The results are shown in FIG. 2. The left side of FIG. 2 shows results of examining cell adhesion due to an RhoA inhibitor by assessing the number of adhering cells with CellTiter-Glo®. It was found as a result that the number of adhering cells significantly increased when an RhoA inhibitor C3 was added in comparison to the control. The right side of FIG. 2 is a result of measuring the activity of adhesion-related molecules after the addition of an RhoA inhibitor by Western blot. It was possible to verify that the addition of a RhoA inhibitor C3 promotes phosphorylation of adhesion-related molecules FAK and paxillin.

Example 1

Examination of Cell Adhesion Due to MLC Phosphorylation Inhibitor

The present Example examined the involvement of MLC, which is downstream of a Rho-ROCK pathway and phosphorylated by the activation thereof, in cell adhesion.

(Materials and Method)

In short, cell adhesion due to a p-MLC inhibitor was examined by assessing the number of adhering cells with CellTiter-Glo®. Further, the activity of adhesion-related molecules after the addition of an RhoA inhibitor was measured by Western blot.

(Examination of Number of Adhering Cells).

The number of adhering cells was analyzed by using CellTiter-Glo®. First, cultured monkey corneal endothelial cells were seeded onto a 96 well plate at 5000 cells/well in DMEM (Gibco-Invitrogen) to which blebbistatin (MILLIPORE, catalog number: 203391) was added such that the final concentration would be 100 µM. DMEM (Gibco-Invitrogen) was used as a control. The cells were washed with PBS(−) after three hours from seeding. PBS(−) was removed by tapping. The CellTiter-Glo® reagent and medium returned to room temperature were added thereto at 1:1 and shaken for 10 minutes in the dark. Furthermore, the mixture was left standing for 10 minutes for it to reach equilibrium. The mixture was then transferred to a white plate to measure absorbance.

(Western Blot)

DMEM (Gibco-Invitrogen) to which blebbistatin was added such that the final concentration would be 100 µM and cultured monkey corneal endothelial cells were seeded. Over time, i.e., 0, 1, 3, and 24 hours thereafter, proteins extracted with RIPA buffer were subjected to electrophoresis with 7.5% polyacrylamide. DMEM (Gibco-Invitrogen) was used as a control. The separated protein was transcribed onto a PVDF membrane (PALL LIFE SCIENCE, catalog number: EH-2222). Blocking procedure was carried out by incubating a Tris buffered saline (10 mM Tris-HCl, pH 7.4, 100 mM NaCl) supplemented with 0.1% (vol/vol) polyethylene sorbitan monolaurate (Nacalai Tesque, catalog number: 28353-85) (TBS-T) and 5% non-fat dry milk (CELL SIGNALING, catalog number: 9999) and the blotted membrane for one hour. The membrane was then immersed in TBS-T supplemented with antibodies against Phospho Paxillin (Tyr118) Antibody (CELL SIGNALING, catalog number: 2541), GAPDH (14C10) Rabbit mAb (CELL SIGNALING, catalog number: 2118) and diluted 1000-fold, and reacted for 1 hour at room temperature. After washing three times with TBS-T, a mouse-IgG antibody HRP complex (CELL SIGNALING, catalog number: 7074P2) and rabbit-IgG antibody HRP complex (GE Healthcare, catalog number: NA934) were incubated, washed, and then made to emit light with ECL-ADVANCE (GE Healthcare Japan, catalog number: RPN2135V) to detect a band.

(Results)

Figure 3:
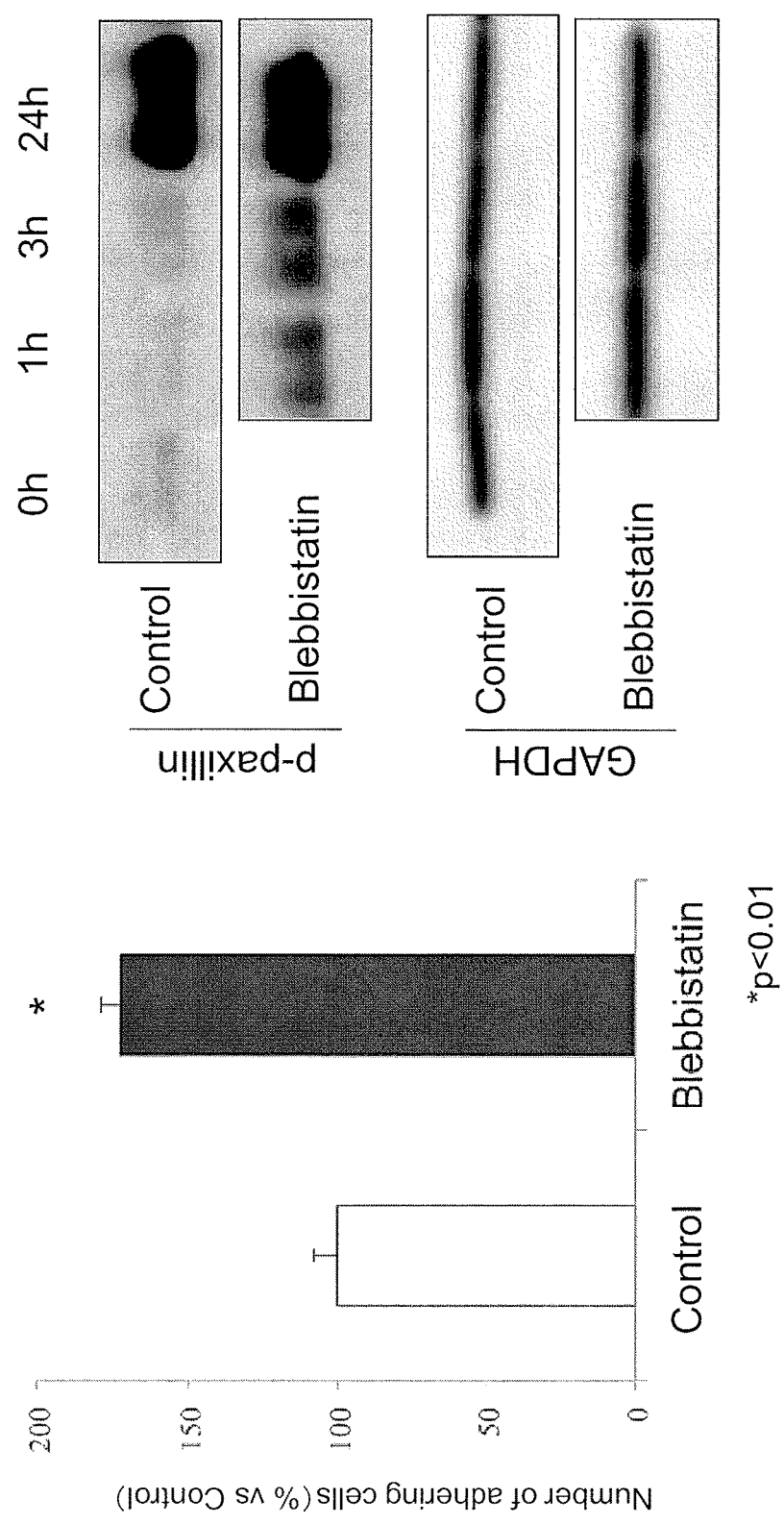
FIG. 3 shows results of examining cell adhesion due to an MLC phosphorylation inhibitor. The involvement of MLC, which is downstream of a Rho-ROCK pathway and phosphorylated by the activation thereof, in cell adhesion was examined. The left diagram shows results of examining cell adhesion due to a p-MLC inhibitor by assessing the number of adhering cells with CellTiter-Glo®. The results show that the number of adhering cells significantly increased when a p-MLC inhibitor blebbistatin was added in comparison to the control. The right diagram shows results of measuring the activity of adhesion-related molecules after the addition of a p-MLC inhibitor by Western blot. It was possible to verify that an adhesion related molecule paxillin is phosphorylated at an early stage by the addition of blebbistatin.

The results are shown in FIG. 3. The left side of FIG. 3 is a result of examining cell adhesion due to a p-MLC inhibitor by assessing the number of adhering cells with CellTiter-Glo®. It was found as a result that the number of adhering cells significantly increased when a p-MLC inhibitor blebbistatin was added in comparison to the control. The right side of FIG. 3 is a result of measuring the activity of adhesion-related molecules after the addition of a p-MLC inhibitor by Western blot. It was possible to verify that an adhesion-related molecule paxillin is phosphorylated at an early stage by the addition of blebbistatin.

Example 2

Transplantation of Cultured Corneal Endothelial Cells Used in Combination with Blebbistatin The present Example studied the state after transplantation of cultured corneal endothelial cells used in combination with blebbistatin.

(Materials and Methods)

All rabbit corneal tissues used in this experiment were purchased for use as research eye balls from a rabbit euthanized for other research purposes (Oriental Bioservice).

(Cell Culture)

In primary culture of rabbit corneal endothelial cells, a Descemet's membrane including an endothelial cell layer was detached from a corneal tissue and 0.5 ml of Accutase (catalog number: AT104, Innovative Cell Technologies) was used for each eye, and incubated at 37° C. by using a water bath. After 20 minutes, a culture medium was added and pipetting was performed. The sample was centrifuged at 1200 rpm for 3 minutes to remove the supernatant. A culture medium was then added to a precipitated corneal endothelial cell mass for admixing. The entire amount was seeded on a 12-well plate coated with FNC Coating Mix (catalog No.: 0407; Athena Enzyme Systems, Baltimore, Md., USA). DMEM (catalog No.: 12320; Gibco-Invitrogen), to which 10% FBS, 1% Penicillin-Streptomycin Mixed Solution (catalog number: 26252-94; Nacalai Tesque), and 2 ng/ml basic fibroblast growth factor, catalog number: 13256-029; bFGF; Invitrogen) were added, was used as a culture medium.

A medium was exchanged every other day. Subculture was performed when 50 to 80% confluence was reached. With respect to the subculturing method, cells were washed with $Ca^{2+}Mg^{2+}$-free PBS (PBS−; Nissui Pharmaceutical Co., Ltd., Tokyo, Japan), and 0.05% Trypsin-EDTA (catalog No.: 25300-054; Invitrogen) was added and incubated at 37° C. for 3 minutes. Cells were detached and collected from the plate. After the cells were centrifuged at 1500 rpm for 3 minutes, a culture medium was added to make a cell suspension. Cells were seeded on a plate coated with FNC Coating Mix at a density of 1:2-3.

(Transplantation)

Rabbit corneal endothelial cells were detached with a soft tapered needle (Inami, M-563S) to make a bullous keratopathy model. Subsequently, 5.0×10⁵ cultured rabbit corneal endothelial cells were suspended in 200 μl of Dulbecco's Modified Eagle Medium (DMEM) with blebbistatin adjusted to a final concentration of 10 μM. The suspension was injected into the anterior chamber and the corneal surface was maintained in a face-down position for three hours. A group injected with 5.0×10⁵ rabbit corneal endothelial cells suspended into 200 μl of Dulbecco's Modified Eagle Medium (DMEM) with Y-27632 adjusted to a final concentration of 100 μM in the anterior chamber, a group subjected only to scraping off of corneal endothelial cells, and a group injected with 5.0×10⁵ rabbit corneal endothelial cells suspended in a 200 μl of Dulbecco's Modified Eagle Medium (DMEM) into the anterior chamber were used as comparison groups.

(Results)

Figure 4:
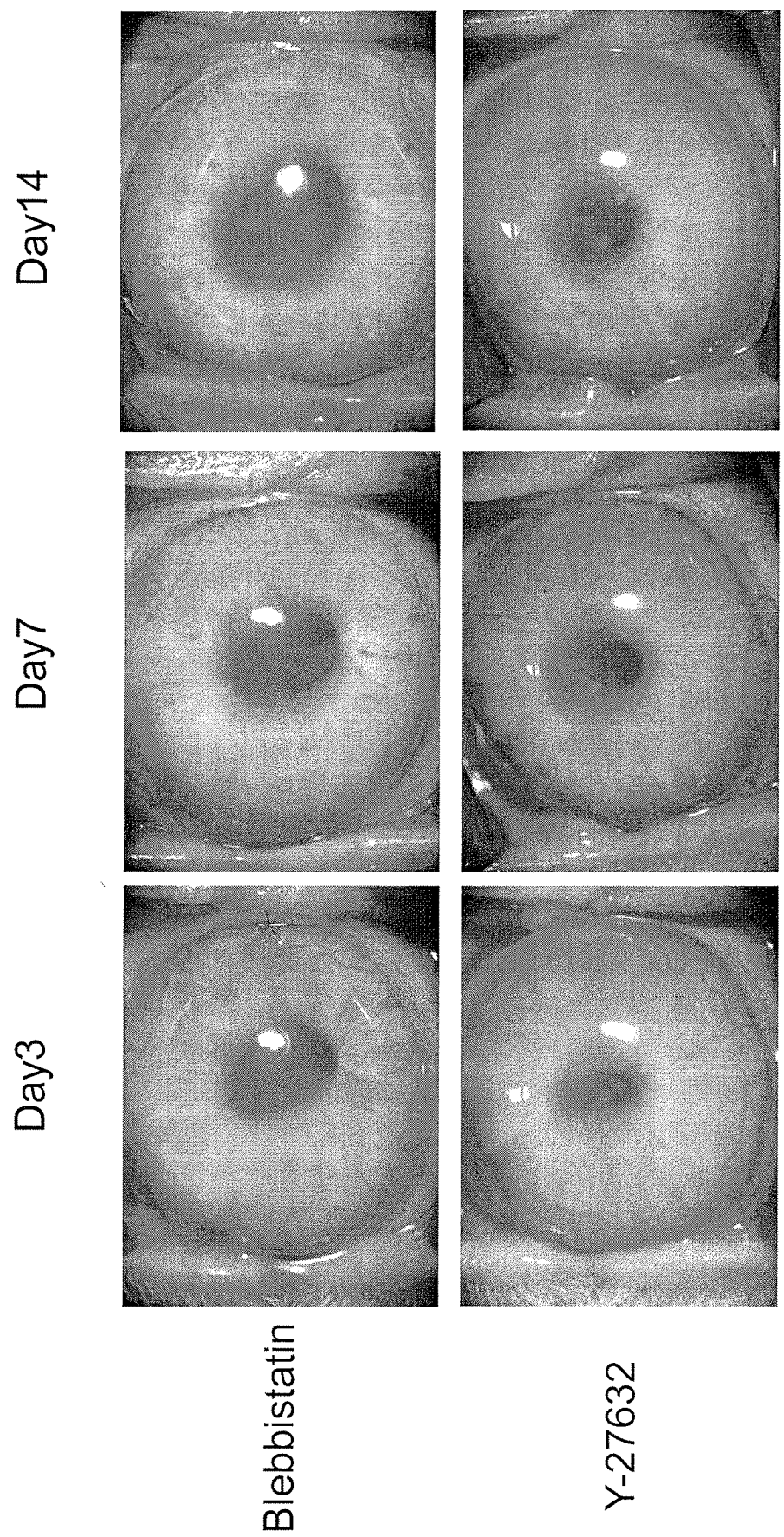
FIG. 4 shows pictures of the anterior ocular section after transplantation of cultured corneal endothelial cells used in combination with blebbistatin. From the left, pictures of the day 3, day 7 and day 14 after treatment are shown. The top row shows a rabbit bullous keratopathy model eye with the corneal endothelium scraped off, whose anterior chamber was injected with $5.0 \times 10^5$ cultured rabbit corneal endothelial cells suspended in 200 µl of Dulbecco's Modified Eagle Medium (DMEM) having blebbistatin adjusted to a final concentration of 10 µM, which was maintained in a face-down position for three hours. The bottom row similarly shows an eye, whose anterior chamber was injected with $5.0 \times 10^5$ cultured rabbit corneal endothelial cells suspended in 200 µl of Dulbecco's Modified Eagle Medium (DMEM) having Y-27632 adjusted to a final concentration of 100 µM, which was maintained in a face-down position for three hours.
Figure 5:
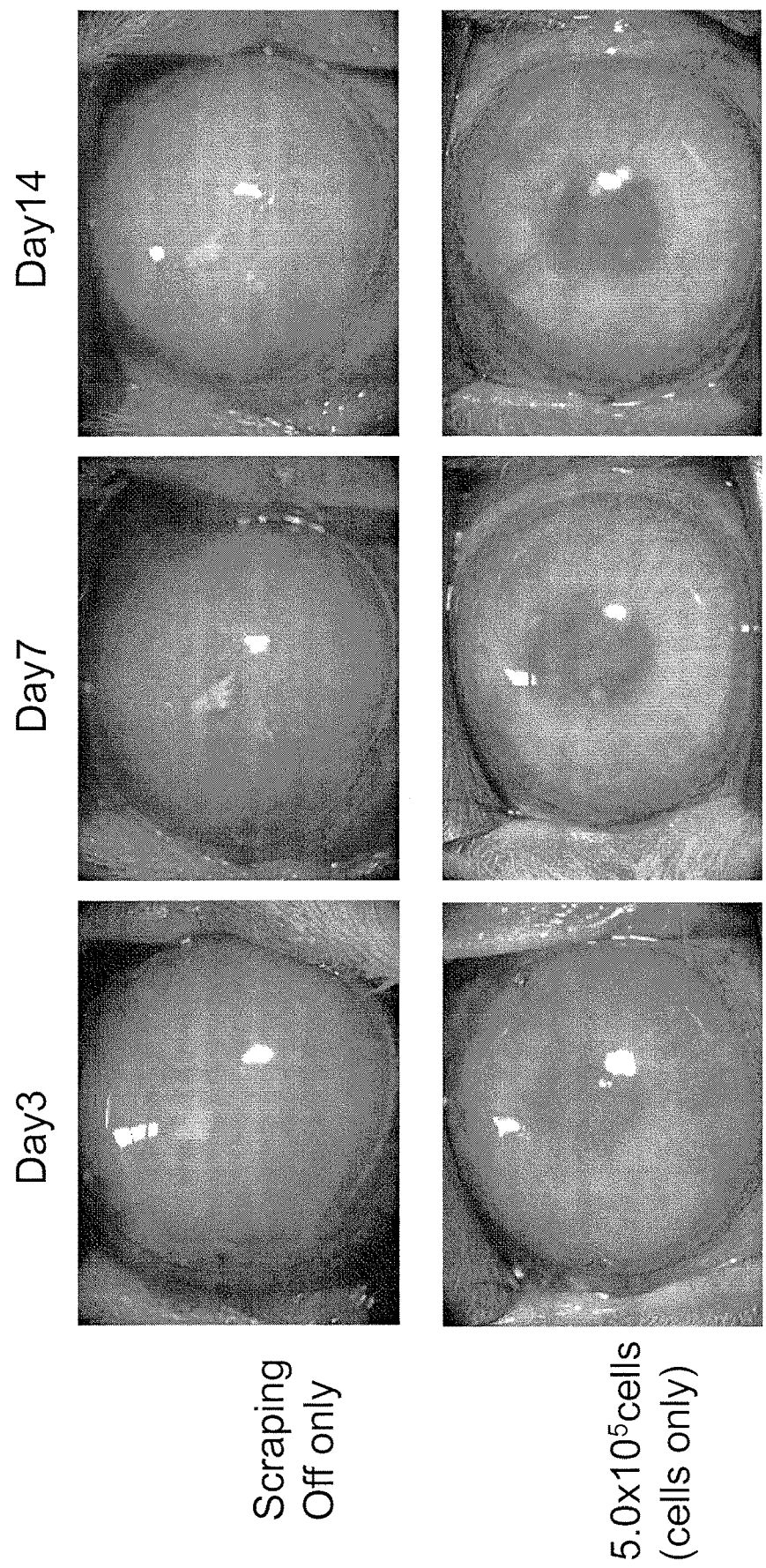
FIG. 5 shows, on the top row, pictures of the anterior ocular section of a rabbit bullous keratopathy model with the corneal endothelium scraped off as the control. The bottom row shows a rabbit bullous keratopathy model eye with the corneal endothelium scraped off, whose anterior chamber was injected with $5.0 \times 10^5$ cultured rabbit corneal endothelial cells suspended in 200 µl of Dulbecco's Modified Eagle Medium (DMEM), which was maintained in a face-down position for three hours. From the left, picture of the day 3, day 7, and day 14 after treatment are shown.

FIGS. 4-5 show pictures of the anterior ocular section after transplantation of cultured corneal endothelial cells used in combination with blebbistatin. The top row of FIG. 4 shows results from using blebbistatin (day 3, day 7, and day 14). The bottom row of FIG. 4 shows results from using Y-27632 (day 3, day 7, and day 14). The top row of FIG. 5 shows results of only scraping (day 3, day 7, and day 14) and the bottom row of FIG. 5 shows results of only cells (day 3, day 7, and day 14) as controls. It was found, as shown, that combined use of blebbistatin is excellent as with Y-27632.

Example 3

State After Transplantation of Cultured Corneal Endothelial Cells Used in Combination with Blebbistatin The present Example measured the thickness of cornea, intraocular pressure and immunohistological examination after transplantation of cultured corneal endothelial cells used in combination with blebbistatin.

(Measurement of Thickness of Cornea and Intraocular Pressure)

The thickness of rabbit corneas after transplantation of cultured corneal endothelial cells was measured with an ultrasound pachymeter (SP-2000; Tomey, Nagoya, Japan). Further, intraocular pressure was measured with Tonovet (catalog number: TV01, ME Technica).

(Immunohistological Examination)

A rabbit was euthanized to extract the cornea. ZO-1 and Na⁺/K⁺-ATPase were used as a function associated marker and immunostaining was performed. The sample was observed with a fluorescence microscope. For tissue staining inspection, it was immobilized at room temperature (RT) for 10 minutes with 4% paraformaldehyde and incubated for 30 minutes with 1% bovine serum albumin (BSA). Immunohistochemical analysis was performed on adhesion binding associated protein ZO-1 (Zymed Laboratories, Inc., South San Francisco, Calif.), pumping function associated protein Na⁺/K⁺-ATPase (Upstate Biotec, Inc., Lake Placid, N.Y.) and actin. For secondary antibodies, Alexa Fluor® 488 labeling or Alexa Fluor® 594 labeling goat antimouse IgG (Life Technologies) diluted at 1:2000 was used. Actin was stained by using a 1:400 dilution of Alexa Fluor® 488 labeled phalloidin (Life Technologies). Cellular nuclei were then stained with DAPI (Vector Laboratories, Inc., Burlingame, Calif.). Slides were then observed with a fluorescent microscope (TCS SP2 AOBS; Leica Microsystems, Welzlar, Germany).

(Results)

Figure 6:
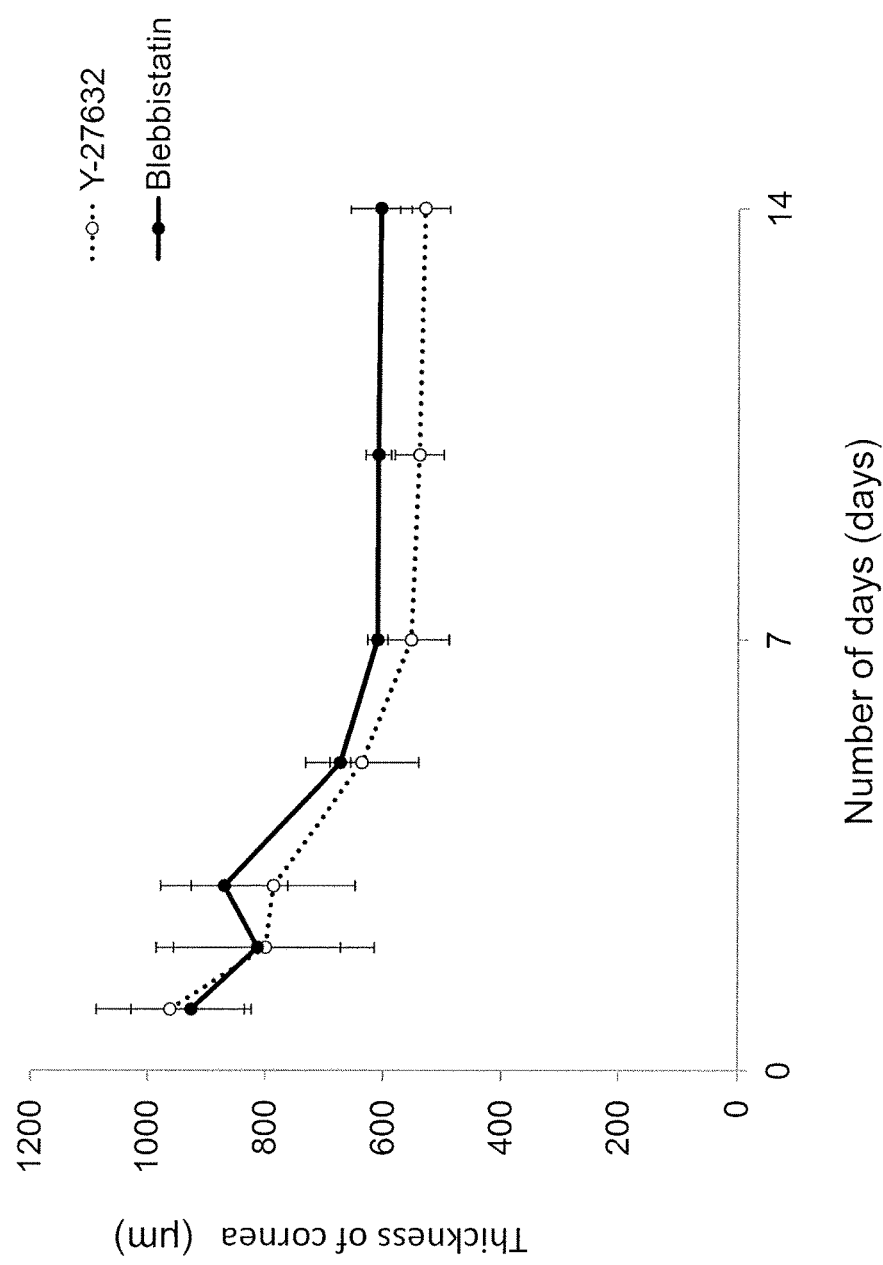
Figure 7:
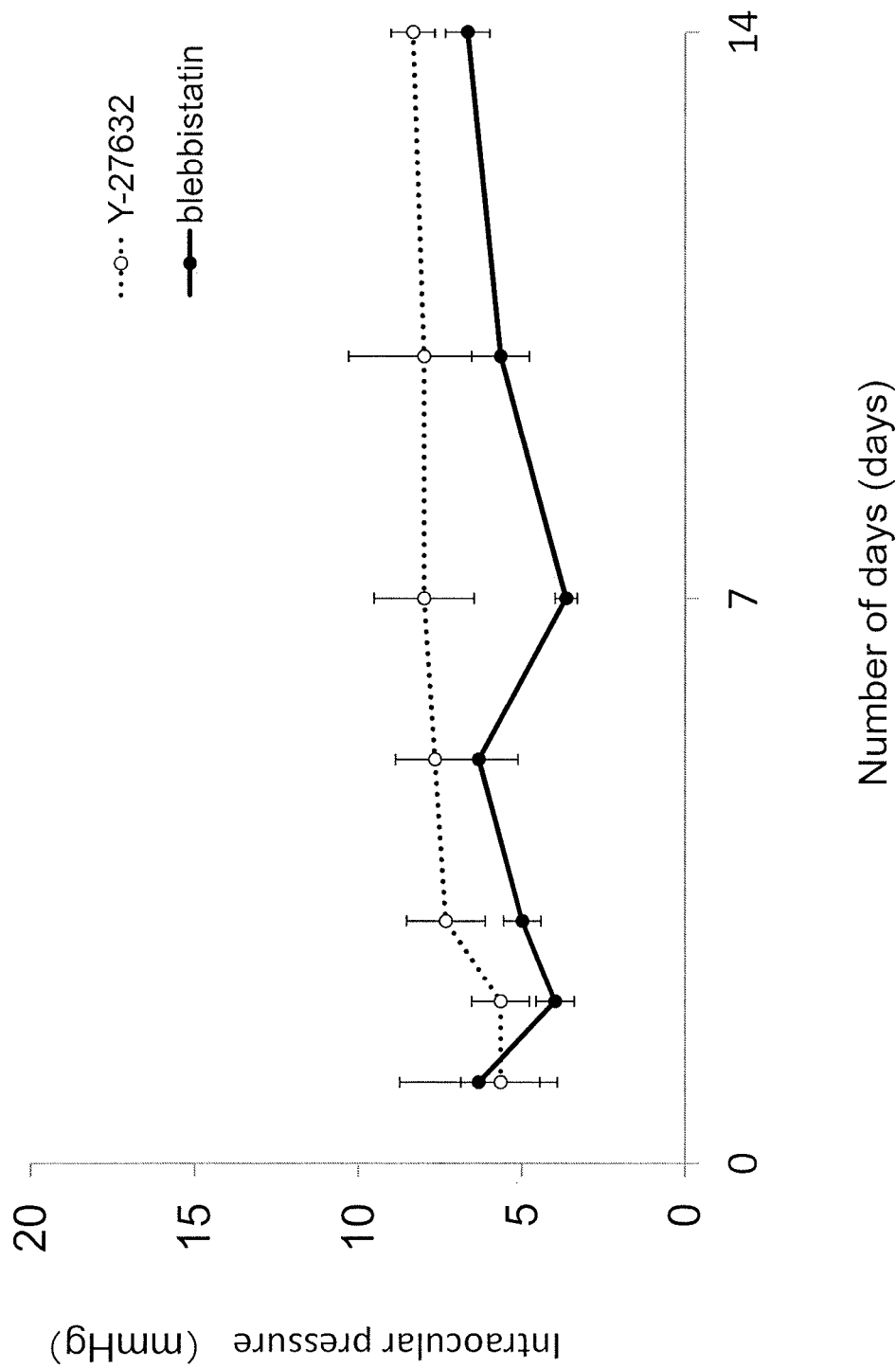
Figure 8:
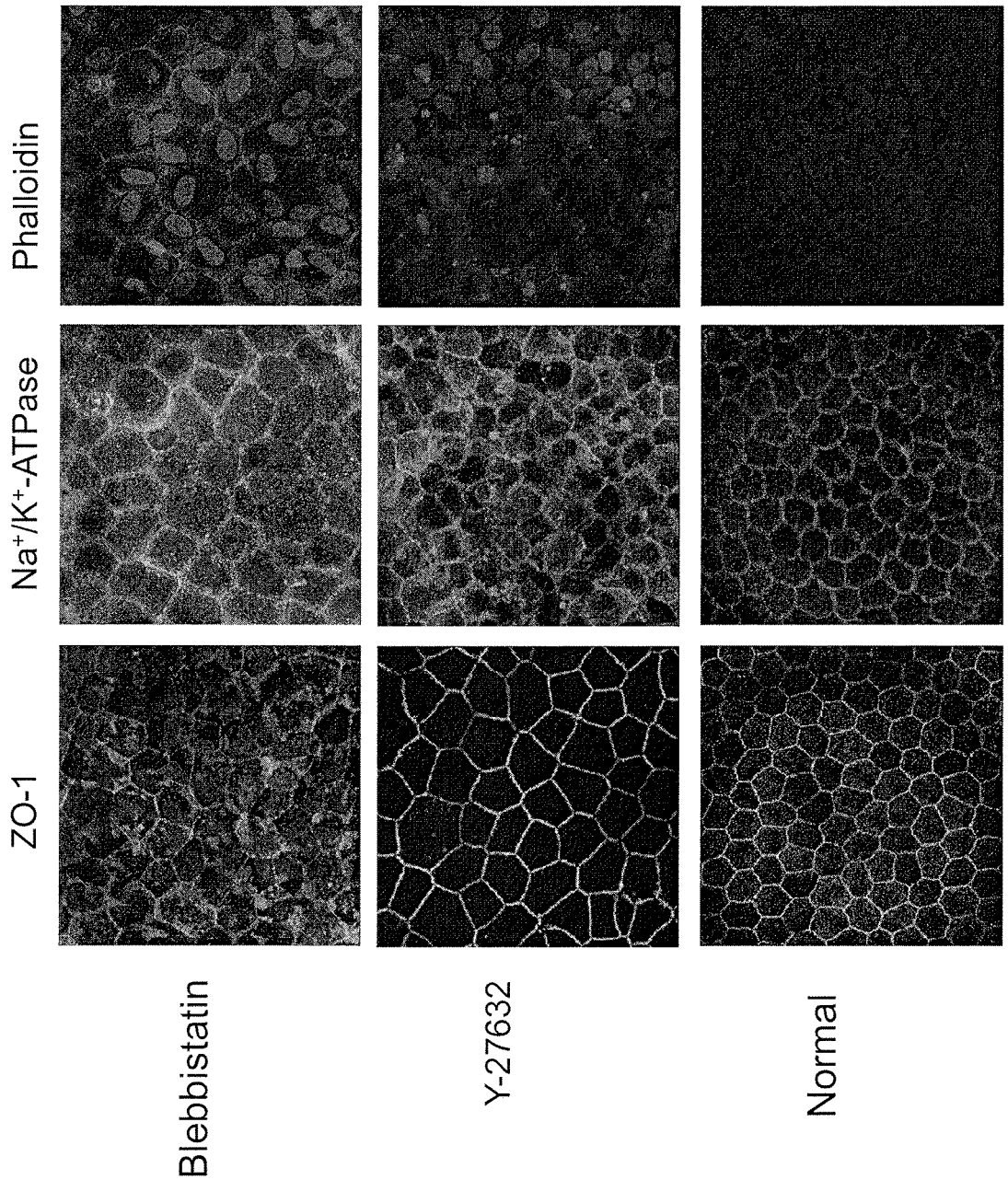
FIG. 8 shows the results of immunohistological examination after transplantation of cultured corneal endothelial cells used in combination with blebbistatin. From the left, results of staining with ZO-1, $Na^+/K^+$-ATPase and phalloidin which represent cellular functions. The results are, from the top row, for blebbistatin, Y-27632, and normal (control without treatment).

Results are shown in FIGS. 6-8. FIG. 6 shows the thickness of a cornea after transplantation of cultured corneal endothelial cells used in combination with blebbistatin. FIG. 7 shows the intraocular pressure after transplantation of cultured corneal endothelial cells used in combination with blebbistatin. FIG. 8 shows the results of immunohistological examination after transplantation of cultured corneal endothelial cells used in combination with blebbistatin.

Example 4

Transplantation of Cultured Corneal Endothelial Cells Used in Combination a Low Concentration of Blebbistatin A rabbit bullous keratopathy model eye with the corneal endothelium scraped off was injected with 5.0×10⁵ cultured rabbit corneal endothelial cells suspended in 200 μl of Dulbecco's Modified Eagle Medium (DMEM) with blebbistatin adjusted to a final concentration of 1 μM and 3 μM into the anterior chamber as in Example 3. The model eye was maintained in a face down position for three hours to examine recovery of corneal transparency and regeneration of corneal endothelium.

(Immunohistological Examination)

A rabbit was euthanized to extract the cornea. ZO-1, Na⁺/K⁺-ATPase and N-cadherin were used as a function associated marker and immunostaining was performed. The sample was observed with a fluorescence microscope. For tissue staining inspection, it was immobilized at room temperature (RT) for 10 minutes with 4% paraformaldehyde and incubated for 30 minutes with 1% bovine serum albumin (BSA). Immunohistochemical analysis was performed on adhesion binding associated protein ZO-1 (Zymed Laboratories, Inc., South San Francisco, Calif.), pumping function associated protein Na⁺/K⁺-ATPase (Upstate Biotec, Inc., Lake Placid, N.Y.), N-cadherin (BD Transduction Laboratories, catalog number: 610920) and actin. For secondary antibodies, Alexa Fluor® 488 labeling or Alexa Fluor® 594 labeling goat antimouse IgG (Life Technologies) diluted at 1:2000 was used. Actin was stained by using a 1:400 dilution of Alexa Fluor® 488 labeled phalloidin (Life Technologies). Cellular nuclei were then stained with DAPI (Vector Laboratories, Inc., Burlingame, Calif.). Slides were then observed with a fluorescent microscope (TCS SP2 AOBS; Leica Microsystems, Welzlar, Germany).

(Results)

Figure 9:
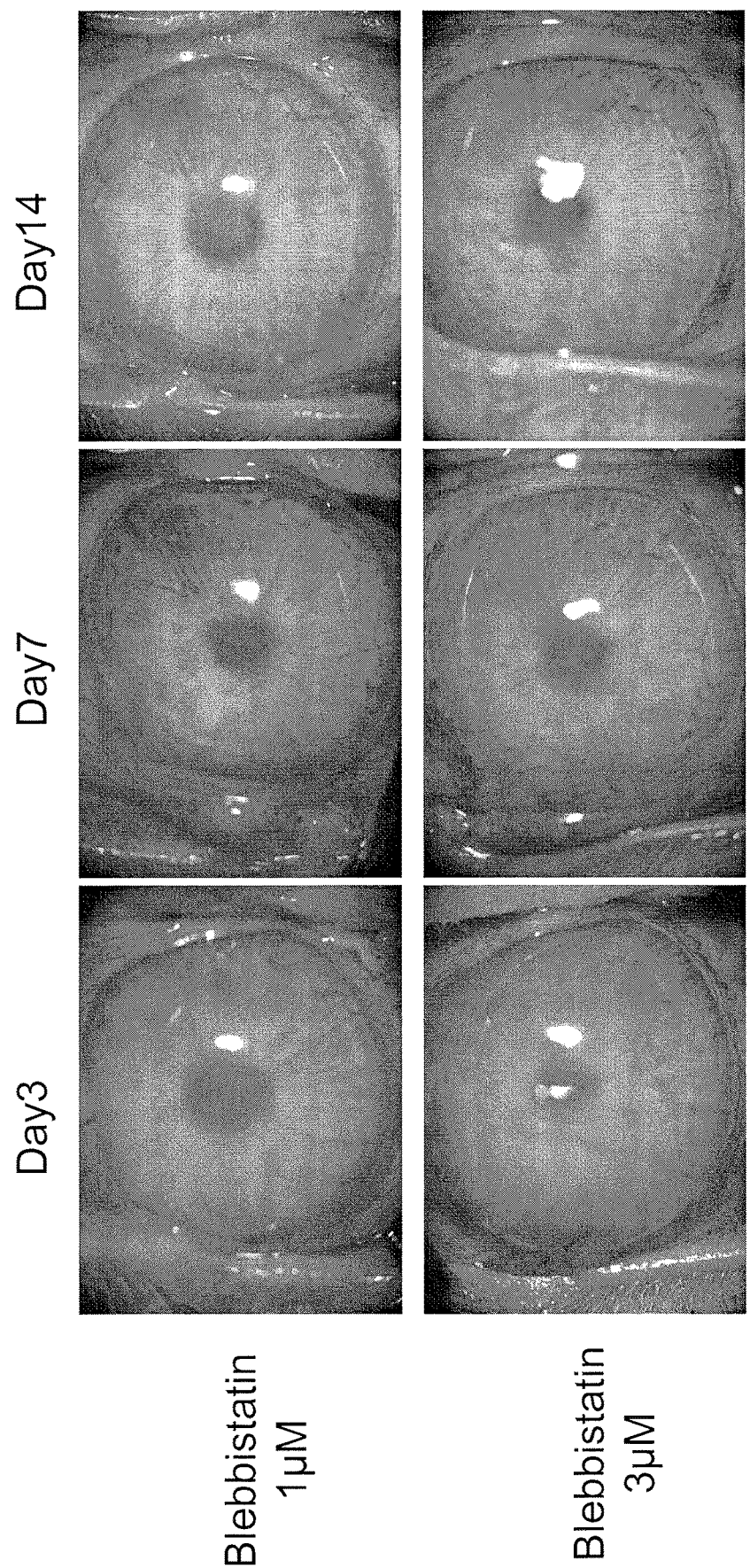
FIG. 9 shows pictures of the anterior ocular section after transplantation of cultured corneal endothelial cells used in combination with blebbistatin. From the left, pictures of the day 3, day 7 and day 14 after treatment are shown. The top row shows a rabbit bullous keratopathy model eye with the corneal endothelium scraped off, whose anterior chamber was injected with $5.0 \times 10^5$ cultured rabbit corneal endothelial cells suspended in 200 μl of Dulbecco's Modified Eagle Medium (DMEM) having blebbistatin adjusted to a final concentration of 1 μM, which was maintained in a face-down position for three hours. The bottom row similarly shows an eye, whose anterior chamber was injected with $5.0 \times 10^5$ cultured rabbit corneal endothelial cells suspended in 200 μl of Dulbecco's Modified Eagle Medium (DMEM) having blebbistatin adjusted to a final concentration of 3 μM, which was maintained in a face-down position for three hours.
Figure 10:
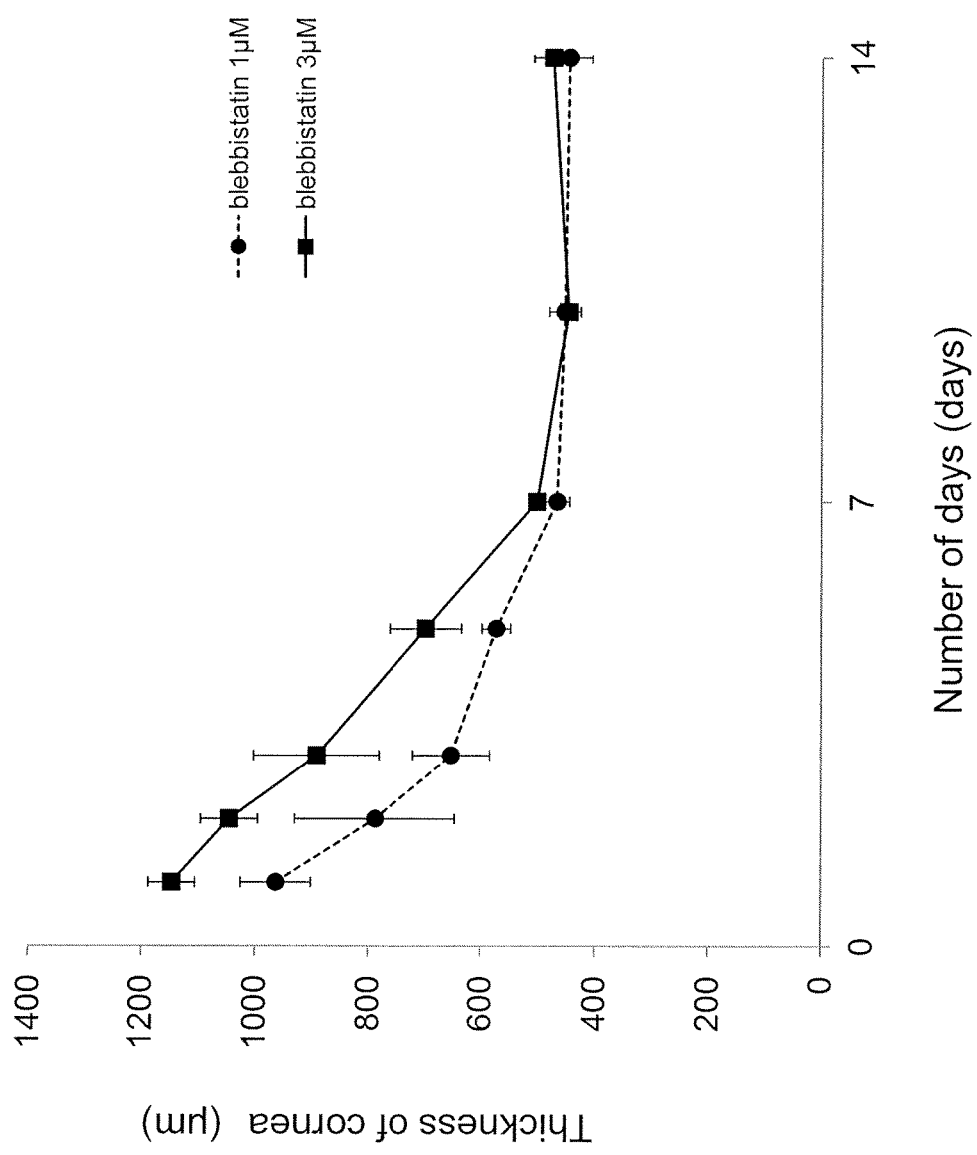
FIG. 10 shows the thickness of cornea after transplantation of cultured corneal endothelial cells used in combination with blebbistatin. The X axis indicates the number of days (days) and the Y axis indicates the thickness of cornea (μm). The dotted line and the black circles indicate 1 μM of blebbistatin and the thick line and the black squares indicate 3 μM of blebbistatin.
Figure 11:
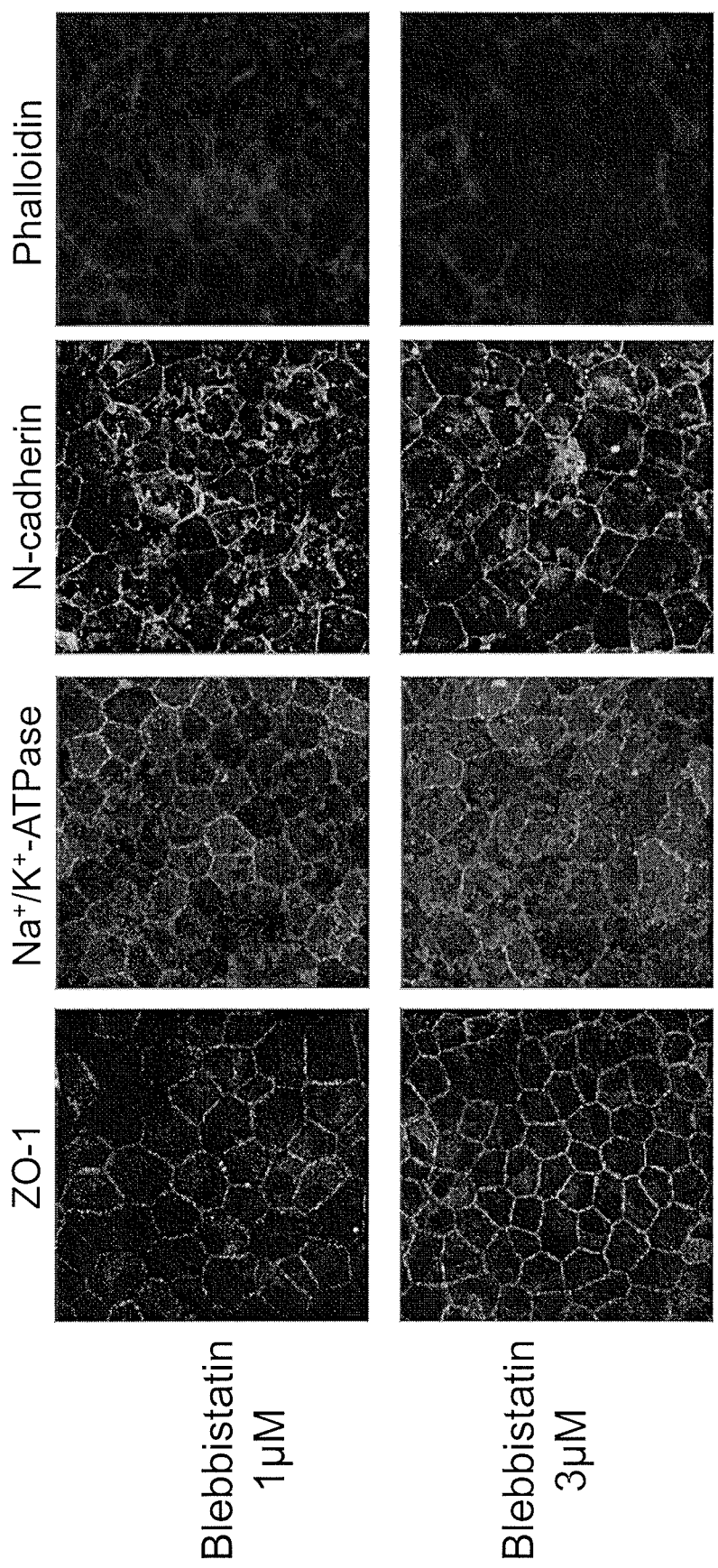
FIG. 11 shows results of immunohistological examination after transplantation of cultured corneal endothelial cells used in combination with blebbistatin. From the left, results of staining with ZO-1, $Na^+/K^+$-ATPase, N-cadherin, and phalloidin, which represent cellular functions. The results are, from the top row, for 1 μM and 3 μM of blebbistatin.

The results are shown in FIGS. 9-11. FIG. 9 shows pictures of the anterior ocular section, FIG. 10 shows the thickness of cornea, and FIG. 11 shows results of immunohistological examination after transplantation of cultured corneal endothelial cells.

(Discussion)

Figure 12:
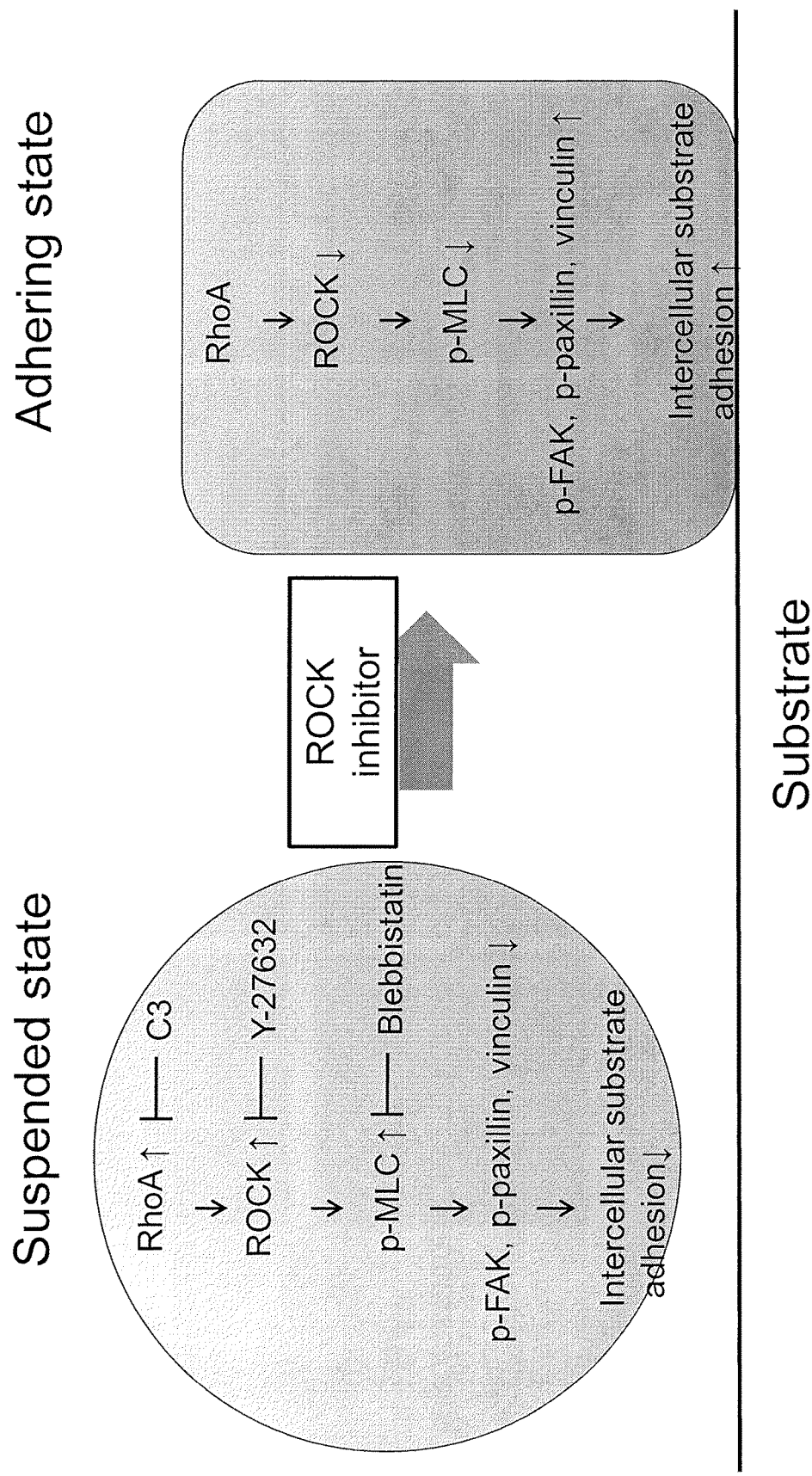
FIG. 12 shows a scheme for promoting cell adhesion by regulating Rho/ROCK/MLC pathways elucidated by the present invention. In view of the results of the present Example, it was conjectured that for cells in a suspended state, the activity of RhoA increases and the activity of ROCK increases and the phosphorylation of MLC progresses to suppress the phosphorylation of adhesion-related molecules FAK and paxillin and expression of vinculin, such that intercellular substrate adhesion is inhibited. In addition, the addition of blebbistatin resulted in suppression of the MLC phosphorylation activity to suppress actin contraction to promote the activity of adhesion-related molecules, such that substrate adhesion of corneal endothelial cells is promoted.

In view of these experimental results as shown in FIG. 12, it can be conjectured that, for cells in a suspended state, when the activity of RhoA increases, the activity of ROCK also increases and the phosphorylation of MLC progresses to suppress the expression of vinculin and phosphorylation of adhesion-related molecules FAK and paxillin, such that intercellular substrate adhesion is inhibited. In addition, the addition of blebbistatin resulted in suppression of the MLC phosphorylation activity to suppress actin contraction to promote the activity of adhesion-related molecules, such that substrate adhesion of corneal endothelial cells is promoted. Furthermore, it was demonstrated that therapy was possible at a lower concentration relative to Y-27632.

As described above, the present invention is exemplified by the use of its preferred Embodiments. However, it is understood that the scope of the present invention should be interpreted solely based on the claims. It is also understood that any patent, any patent application, and any references cited in the present specification should be incorporated by reference in the present specification in the same manner as the contents are specifically described therein.

INDUSTRIAL APPLICABILITY

The present invention provides an industrially applicable technique (in cell culture industry, pharmaceutical industry etc.) related to a therapeutic or prophylactic drug for a disease, disorder or condition of a corneal endothelium, comprising a myosin II-specific inhibitor, particularly those using corneal endothelial cells.

The invention claimed is:

1. A method for treating a disease, disorder or condition of a corneal endothelium in a subject, wherein the disease, disorder or condition is bullous keratopathy, and wherein the method consists essentially of a step of administering an effective amount of blebbistatin in conjunction with a corneal endothelial cell to the subject.

2. The method of claim 1 wherein the blebbistatin is administered as eye drops.

3. The method of claim 1, wherein the disease, disorder or condition is due to a trauma or a surgical operation.

4. The method of claim 1, wherein the disease, disorder or condition is selected from the group consisting of photophobia, blurred vision, visual impairment, ophthalmalgia, epiphora, hyperemia, pain, eye discomfort, diminished contrast, glare, edema of the corneal stroma and corneal turbidity in bullous keratopathy.

5. The method of claim 1, wherein the corneal endothelium is from a primate.

6. The method of claim 1, wherein the corneal endothelium is from a human.

7. The method of claim 1, wherein the blebbistatin is administered so that the blebbistatin is at a concentration of about 1 µM to about 10 µM in the anterior chamber.

8. The method of claim 1, further comprising administering an additional pharmaceutical ingredient to the subject.

* * * * *